(12) United States Patent
Tainsky et al.

(10) Patent No.: US 9,797,906 B2
(45) Date of Patent: Oct. 24, 2017

(54) DETECTORS OF SERUM BIOMARKERS FOR PREDICTING OVARIAN CANCER RECURRENCE

(71) Applicants: Michael Tainsky, Southfield, MI (US); Madhumita Chatterjee, Lake Orion, MI (US); Gregory Dyson, Northville, MI (US); Nancy Levin, Birmingham, MI (US)

(72) Inventors: Michael Tainsky, Southfield, MI (US); Madhumita Chatterjee, Lake Orion, MI (US); Gregory Dyson, Northville, MI (US); Nancy Levin, Birmingham, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 14/398,773

(22) PCT Filed: May 6, 2013

(86) PCT No.: PCT/US2013/039658
§ 371 (c)(1),
(2) Date: Nov. 4, 2014

(87) PCT Pub. No.: WO2013/166480
PCT Pub. Date: Nov. 7, 2013

(65) Prior Publication Data
US 2015/0139980 A1    May 21, 2015

Related U.S. Application Data

(60) Provisional application No. 61/642,488, filed on May 4, 2012.

(51) Int. Cl.
| | |
|---|---|
| *G01N 33/573* | (2006.01) |
| *G01N 33/574* | (2006.01) |
| *G01N 33/564* | (2006.01) |
| *C07K 16/32* | (2006.01) |

(52) U.S. Cl.
CPC ....... *G01N 33/57449* (2013.01); *C07K 16/32* (2013.01); *G01N 33/564* (2013.01); *G01N 2800/52* (2013.01); *G01N 2800/54* (2013.01)

(58) Field of Classification Search
None
See application file for complete search history.

(56) References Cited

U.S. PATENT DOCUMENTS

2003/0223997 A1* 12/2003 Challita-Eid .......... C07K 16/30
424/155.1
2011/0190149 A1*  8/2011 Tainsky ........... G01N 33/57407
506/9

* cited by examiner

*Primary Examiner* — Lei Yao
(74) *Attorney, Agent, or Firm* — Kohn & Associates PLLC

(57) ABSTRACT

Polypeptide marker antigens for detecting the presence of autoantibody biomarkers associated with ovarian cancer recurrence, each of the polypeptide marker antigens binding specifically to at least one autoantibody marker. An antibody binding assay for detecting the presence of autoantibody biomarkers associated with ovarian cancer recurrence, and methods for performing the assay. Methods for determining ovarian cancer recurrence in an ovarian cancer patient. A method for isolating antibodies specific for ovarian cancer by their affinity to the polypeptide marker antigens, and antibodies isolated by that method.

5 Claims, 10 Drawing Sheets

SEQUENCE LISTING

<160> NUMBER OF SEQ IDS NOS: 10

<210> SEQ ID NO 1
<211> LENGTH: 24
<212> TYPE: PRT
<213> ORGANISM: Homo sapiens

<400> SEQUENCE: 1

Glu Val Asp Val Arg Arg Glu Asp Leu Val Glu Glu Ile Lys Arg Arg
1               5                   10                  15

Thr Gly Gln Pro Leu Cys Ile Cys
            20

<210> SEQ ID NO 2
<211> LENGTH: 8
<212> TYPE: PRT
<213> ORGANISM: Homo sapiens

<400> SEQUENCE: 2

Pro Gly Cys Ser Thr Thr Leu Ser
1               5

<210> SEQ ID NO 3
<211> LENGTH: 11
<212> TYPE: PRT
<213> ORGANISM: Homo sapiens

<400> SEQUENCE: 3

Asn Ser Phe Leu Met Thr Ser Ser Lys Pro Arg
1               5                   10

<210> SEQ ID NO 4
<211> LENGTH: 8
<212> TYPE: PRT
<213> ORGANISM: Homo sapiens

<400> SEQUENCE: 4

Glu Asn Val Leu Val Gln Thr Asn
1               5

<210> SEQ ID NO 5
<211> LENGTH: 4
<212> TYPE: PRT
<213> ORGANISM: Homo sapiens

<400> SEQUENCE: 5

Glu Leu His Asn
1

<210> SEQ ID NO 6
<211> LENGTH: 11
<212> TYPE: PRT
<213> ORGANISM: Homo sapiens

<400> SEQUENCE: 6

Leu Gly Ser Asp Glu Arg Arg His Arg Ala Pro
1               5                   10

<210> SEQ ID NO 7
<211> LENGTH: 18
<212> TYPE: PRT
<213> ORGANISM: Homo sapiens

<400> SEQUENCE: 7

-continued

```
Val Asp Glu Glu Asp Met Met Asn Gln Val Leu Gln Arg Ser Ile Ile
1               5                   10                  15

Asp Gln

<210> SEQ ID NO 8
<211> LENGTH: 28
<212> TYPE: PRT
<213> ORGANISM: Homo sapiens

<400> SEQUENCE: 8

Val Gln Ala Gln Gln Arg Ser Ala Pro Ala Arg Ala Ala Arg Ala Gly
1               5                   10                  15

His Pro Glu Ala Gly Ala Gly Met Glu Gly Ala Gly
            20                  25

<210> SEQ ID NO 9
<211> LENGTH: 10
<212> TYPE: PRT
<213> ORGANISM: Homo sapiens

<400> SEQUENCE: 9

Pro Lys Thr Met Thr Gln Asn Ser Phe Gly
1               5                   10

<210> SEQ ID NO 10
<211> LENGTH: 6
<212> TYPE: PRT
<213> ORGANISM: Homo sapiens

<400> SEQUENCE: 10

Tyr Ala Cys Leu Lys Asp
1               5
```

DETECTORS OF SERUM BIOMARKERS FOR PREDICTING OVARIAN CANCER RECURRENCE

GRANT INFORMATION

Research in this application was supported in part by grants from the National Institutes of Health (NIH Grant Nos. R21/R33-CA100740 and 1R01CA160541). The Government has certain rights in the invention.

TECHNICAL FIELD

The present invention relates to an assay and method for diagnosing disease. More specifically, the present invention relates to markers and assays for predicting or detecting recurrence of cancer and for enhancing the treatment of recurrent cancer

BACKGROUND OF THE INVENTION

The asymptomatic nature of OVCA together with lack of effective diagnostic screening tools makes the disease extremely difficult to detect at an early stage. Consequently, OVCA is often diagnosed at an advanced stage in approximately 70% of patients (1). Despite an initial response to primary, or "first-line", treatment more than 85% of patients with advanced disease will experience OVCA recurrence after the completion of first-line treatment even with optimal surgical cytoreduction and platinum-based combination chemotherapy (2,3). Patients bearing platinum-sensitive tumors have a relapse-free period of at least 6 months following their last platinum treatment compared to patients bearing platinum resistant tumors who fail to achieve complete response after first-line treatment and relapse in less than 6 months from the completion of therapy (4). Evaluation of effects of primary treatment and the early detection of recurrence in those with platinum-sensitive tumors is an important goal of routine follow-up to improve the life expectancy.

Over the years CA125 has emerged as a useful biomarker for monitoring of OVCA recurrence (5). To date, CA125 is most extensively used in monitoring OVCA during routine follow-up visits because in about 80% of patients an increase in the level of CA125 may be the first indication of relapse that precedes recurrence by 3-5 months (30). Redman and colleagues (6) reported that after two courses of chemotherapy, OVCA patients with CA125 values less than 35 U/ml were more likely to achieve remission of disease with longer median survival. Their analyses revealed that the level of CA125 after two courses of chemotherapy treatment appeared as an independent prognostic factor because it predicted the survival status at 12 months with an overall accuracy of 93%. In another study, level of CA125 was found to be elevated above the normal range in 73% of relapsed patients. In that study, physical and gynecological examinations in combination with CA125 increased the detection of relapse up to 92% (7). The study conducted by Krivak and colleagues (8) indicated that following surgery and 6 cycles of chemotherapy, OVCA patients with persistently abnormal CA125 levels >35 U/ml were 2.45 times more likely to have a disease progression (95% CI: 1.52-3.95, P<0.001) and the risk of death for those patients was more than 2.78 times (95% CI: 1.66-4.65, P<0.001) than those with CA125 less than 35 U/ml. Several studies evaluated the risk of recurrence in epithelial OVCA patients with rising CA125 values below the upper limit of normal (<35 U/ml). Wilder and colleagues (9) reported that OVCA patients who had three progressively rising CA125 levels within a normal range (<35 U/ml) at 1-3 months follow-up intervals were associated with a high risk of tumor recurrence. Eleven out of 100 patients who achieved complete remission after surgery and chemotherapy met the criteria for inclusion in their study and were followed at 1 to 3 month intervals with serial CA125 determinations. All 11 patients developed recurrent cancer within 12-33 months after completion of primary treatment. The recent report from a MRC/EORTC (Medical Research Council/European Organisation for Research and Treatment of Cancer) trial demonstrated that OVCA patients with a rising CA125 who received chemotherapy treatments prior to the appearance of clinical symptoms of recurrence had no mortality benefit (31). The limitation of their study was that it took a long time for them to enroll patients and as a result clinician bias may have been introduced for not registering patients who were considered likely to benefit from early chemotherapy. Furthermore, the lack of a benefit in early treatment has been argued to be a result of enrolling patients with poor prognoses (42).

Although CA125 is the most extensively investigated biomarker for diagnosis and monitoring of OVCA, a variety of other tumor biomarkers have been reported to be useful for monitoring response to therapy or indicating relapse during follow-up visits. Anastasi and colleagues conducted a follow-up retrospective study for survival analysis of 8/32 patients with advanced OVCA by evaluating the levels of human epididymis protein 4 (HE4) and CA125 in the serum samples that were collected at the time of diagnosis and at intervals during 16-20 months after surgery. Their study showed that 5/8 patients had an increase in HE4 level above the cut-off value that preceded the rise of CA125 by 5-8 months. This early increase in HE4 level was associated with the relapse of the disease (10). Another study showed that the level of Osteopontin (OPN), a putative plasma biomarker, increased earlier than CA125 in 90% of the patients developing progressive or recurrent epithelial OVCA (median lead time, 3 months) although its role in predicting clinical response to therapy was considered inferior to CA125 (11). Tassi and colleagues (12) reported significant elevation in the expression of Mammaglobin B (MGB-2), a secretoglobin family member, in epithelial OVCA. Univariate survival analysis on 106 OVCA patients enrolled in their study revealed significant correlation of MGB-2 expression with reduced risks of cancer-related death, recurrence and disease progression (p<0.05). In another study, the utility of a biomarker panel comprised of HE4, MMP7 and Glycodelin was evaluated to predict recurrence in a longitudinal monitoring cohort of 30 patients with advanced OVCA. The results indicated that in 27/30 patients who experienced recurrence following initial response to chemotherapy, this biomarker panel predicted recurrence with a sensitivity of 100% compared to 96% for CA125 alone. In 56% patients, the level of one or more panel biomarkers was elevated 6-69 weeks before the rise in CA125 and prior to other clinical evidence of recurrence (13). Other studies examined the BRCAness profile of sporadic ovarian carcinomas in late stage OVCA patients in which the majority had poorly differentiated grade 3 cancers and serous histology. One such study indicated that 41% (7/17) patients who recurred within first year of diagnosis, had tumors with high expression of PARP, FANCD2 and p53 proteins compared to 19% (29/149) patients in the non-recurrence group whose tumors had low expression of the above 3 proteins (14).

Tumor autoantibodies develop at very early stage, well before the clinical manifestations of the disease because of the activation of humoral immune responses due to the presence of small amounts of tumor associated antigens (TAAs) even at very low tumor burden (15). Thus, antibodies against tumor specific proteins may provide the earliest candidate biomarkers for detecting OVCA as well as for monitoring OVCA during the first-line chemotherapy that will provide a signal for the risk of developing OVCA recurrence.

There is a need for reagents that sensitively and specifically detect autoantibody biomarkers associated with ovarian cancer recurrence, and for methods of using these reagents to predict the recurrence of ovarian cancer. There is also a need for methods of directing OVCA treatment selectively toward patients at risk of recurrence.

SUMMARY OF THE INVENTION

The present invention provides polypeptide marker antigens for detecting the presence of autoantibody biomarkers associated with a risk of ovarian cancer recurrence. Each of the polypeptide marker antigens specifically binds to at least one autoantibody biomarker. The present invention also provides an antibody binding assay for detecting the presence of autoantibody biomarkers associated with a risk of ovarian cancer recurrence. The present invention further provides a method for detecting the presence of autoantibody biomarkers associated with the recurrence of ovarian cancer. The present invention still further provides a method for determining a risk of ovarian cancer recurrence in an ovarian cancer patient. The present invention also provides a method for treating ovarian cancer recurrence in an ovarian cancer patient on the basis of the determined risk of recurrence. The present invention further provides a method for isolating antibodies that bind specifically to epitopes of ovarian cancer tissue or ovarian cancer associated tissue, the antibodies being isolated on the basis of their affinity to the polypeptide maker antigens of the present invention. The present invention still further provides antibodies isolated on the basis of their affinity to the polypeptide marker antigens.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
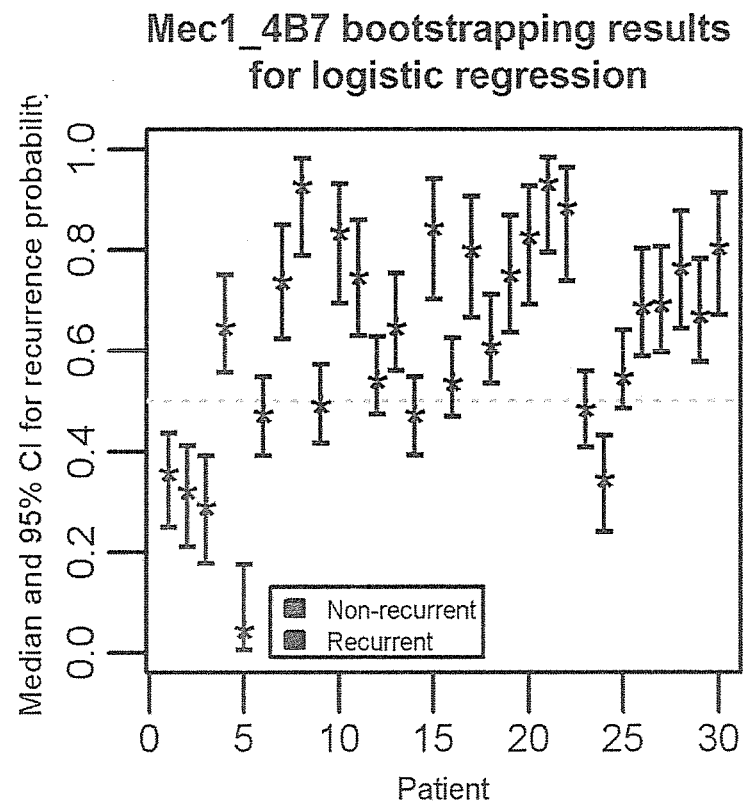
FIG. 1A shows a determination of median and 95% confidence interval of the predicted probability of recurrence of each ovarian cancer patient, based on the performance of polypeptide marker antigen Mec1_4B7, using logistic regression bootstrapped algorithm.

The present invention provides isolated polypeptide marker antigens and methods for their use in predicting and detecting recurrence of ovarian cancer (OVCA). The isolated polypeptide marker antigens are shown to bind specifically to autoantibody biomarkers whose presence in a patient body fluid is associated with the recurrence of OVCA after treatment. The detection of autoantibody biomarkers by their binding to the polypeptide marker antigens is the basis for new tools and methods for determining risk of recurrence, and for earlier detection of recurrence, because the autoantibody biomarkers are present and detectable prior to the presence of symptoms. The determination of risk of recurrence prior to the presence of symptoms in turn enables a method of treatment of recurrent OVCA in which the treatment is administered on the basis of the risk rather than symptoms.

In the following description, the term "recurrence of OVCA" refers to the return of ovarian cancer after treatment, and usually after a period of time during which the cancer cannot be detected. The term "risk of OVCA" refers to both a probability that OVCA will recur in the future and to an actual recurrence of OVCA, such as a subclinical recurrence. The term "biomarker" is defined as a biological molecule found in blood and other body tissues that is an indication of a condition or disease. The term "biomarker autoantibody" is used to indicate autoantibodies associated with the risk of OVCA recurrence. The terms "marker antigen" and "polypeptide marker antigen" refer to a reagent that specifically and detectably binds to at least one patient autoantibody.

The ten isolated polypeptide marker antigens included in the present invention were discovered through use of the robust method of "epitomics" (16 and U.S. Pat. No. 7,863, 004). Epitomics entails the high-throughput cloning of cellular and random polypeptide antigens; the biopanning of patient and control sera against the cloned polypeptides, to discover candidate antigens specifically reactive with disease-associated antibodies; and polypeptide microarray-based serological screening to validate the disease association of the candidate antigen-antibody combinations. More specifically, the polypeptide marker antigens of the present invention were discovered in a study evaluating antigens potentially useful in predicting recurrence in OVCA patients, with a special focus on patients who express CA125 within the normal range (<35 U/ml) and therefore would not be considered by CA125 testing to be at risk of OVCA recurrence. This is a critical patient population, because no biomarker-based or other assays, other than CA125, are currently available to monitor the course of the disease during or after primary chemotherapy treatment. Antibody binding assays including one or more of the ten marker antigens of the present invention can be used to distinguish recurrent from non-recurrent OVCA patients at a median time of 9.07 months prior to clinical recurrence.

It was confirmed that the isolated polypeptide marker antigens of the present invention are useful in detecting autoantibody biomarkers that predict OVCA recurrence prior to the rise in CA125. The predictive value of the panel of ten marker antigens was proven in a sample population of ovarian cancer patients by statistical analyses including logistic regression and classification and regression trees (CART), as detailed in Example 1. The top three marker antigens, SEQ ID NOS: 1, 2, and 3, discriminated between recurrent and nonrecurrent patients with an average sensitivity, specificity and accuracy of 94.7%, 86.7% and 93.3% respectively. Taken as a whole, the panel of ten marker antigens discriminated between recurrent and nonrecurrent patients with an average sensitivity, specificity, and accuracy of 74.8%, 96.0% and 78.3% respectively. These average sensitivity and accuracy values are superior to those determined for immunoassays of the biomarker CA125. The CA125 immunoassays showed a sensitivity and accuracy of 8.0%, and 30.4%, respectively. In Receiver Operating Characteristic Curve (ROC) analyses, as described in Example 1, assays employing each of the 10 marker antigens individually displayed area under the curve (AUC) values greater than the value found for immunoassays of the well-known tumor antigen p53. Thus, each of the ten marker antigens is a valuable individual predictor of OVCA recurrence. In addition, the ten polypeptide marker antigens and subsets thereof are useful as an integrated panel of predictors of OVCA recurrence that is more diverse, and thus more likely to detect rare biomarkers of recurrence, than any single individual marker.

The isolated polypeptide marker antigens of the present invention are useful in antibody binding assays, in which the presence of recurrence-indicating autoantibody biomarkers is detected by their binding to the polypeptide marker antigens. It is likely that the polypeptide marker antigens include epitopes or mimotopes of the original antigens that elicited the production of the patient autoantibody biomarkers. The identification of the original antigens, or the characterization of the patient autoantibodies, is not necessary for the usefulness of the polypeptide marker antigens. The presence of the autoantibody biomarkers alone indicates a risk of OVCA recurrence.

The marker antigens are preferably employed in the form of polypeptides displayed on the surface of bacteriophages in a bacteriophage display system. The usefulness of the polypeptide marker antigens is not limited to the bacteriophage context. They can also be employed as isolated, purified polypeptides. The term "purified" refers to material that is substantially or essentially free from components that normally accompany it as found in its native state. Purity and homogeneity are typically determined using analytical chemistry techniques such as polyacrylamide gel electrophoresis or high performance liquid chromatography. A protein or peptide that is the predominant species present in a preparation is substantially purified. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

The preferred bacteriophage display system is the T7 bacteriophage, most preferably the T7 Select® system available from Novagen (EMD Bioscience Inc: Novagen, San Diego, Calif., USA). Populations of phage expressing and displaying a single marker peptide of the present invention can readily be generated through the insertion of appropriate polypeptide-encoding cDNAs into the phage genome by well-known methods for insertion and for verifying that the correct DNA sequence has been inserted (e.g. Novagen T7 Select® Manual, User Protocol TB178 Rev. D 0311JN, which is also a source of methods for phage amplification). An exemplary method for the PCR amplification and sequencing of inserts in a bacteriophage expression system is found in U.S. Pat. No. 7,964,536, which is incorporated herein by reference in its entirety, at column 37, lines 45-57.

Phage display clones expressing the polypeptide marker antigens of the present invention can readily be generated by one ordinarily skilled in the art of phage display. For example, a clone of T7 bacteriophage expressing a marker antigens of SEQ ID NO: 1 can be generated by synthesizing any cDNA encoding a polypeptide of SEQ ID NO: 1, cloning the cDNA into T7 bacteriophage, cloning the bacteriophage, expanding the clones, and verifying the sequence of the insert in at least one clone. Standard techniques for these procedures are readily available in manuals such as Novagen T7 Select Manual, User Protocol TB178 Rev. D 0311JN.

The isolated polypeptide marker antigens of the present invention can also be obtained by recombinant techniques. Vectors, cloning methods, and purification techniques are readily selected by a skilled artisan from standard laboratory manuals, such as references (51) and (52). For example, a plasmid vector including a polynucleotide encoding a marker antigen, and linked to an appropriate promoter, can be transfected into a host cell line in a calcium phosphate precipitate or charged lipid complex. A viral vector can be packaged in vitro using an appropriate packaging cell line and transduced into a host cell line. The polypeptide marker antigens of this invention can be recovered and purified from recombinant cell cultures by well-known methods including ammonium sulfate or ethanol precipitation, acid extraction, anionic or cationic exchange chromatography, phosphocellulose chromatography, chromatography, and chromatography on hydroxyapatite or affinity columns. High performance liquid chromatography ("HPLC") or affinity purification of a tagged recombinant polypeptide are preferable techniques for purification.

For the detection of the presence of autoantibody biomarkers associated with recurrence of OVCA, the isolated polypeptide marker antigens are preferably spotted or otherwise immobilized on a solid substrate for use in an antibody binding assay. The polypeptide marker antigens serve as capture reagents to bind specifically to patient autoantibody biomarkers. The polypeptide marker antigens can be immobilized in an array including multiple marker antigens, or can be displayed singly, or in any desired configuration. The substrate is preferably a nitrocellulose membrane or a slide coated with nitrocellulose or a nitrocellulose-based polymer. Alternatively, any suitable alternative substrates known in the art can be employed, including a glass, silicon, or plastic slide, a filter, a biochip including signal transducing electronics, an ELISA plate, and a spinning interferometry disc (53). Particulate substrates can also be utilized, for example as fluorescent or nonfluorescent, polystyrene beads and peptide-binding microspheres (54). An advantage of nitrocellulose membranes is that a multiplicity of markers can be deposited in regular arrays by robotic methods, allowing the testing of serum samples against many markers at once; and that many membranes can be simultaneously processed and analyzed for binding of autoantibody biomarkers. It will be understood that all arrays and other arrangements of marker antigen immunoassays must be created in multiple replicates as required for appropriate statistical analysis of results.

Preferably, arrays including the isolated polypeptide marker antigens also include negative control proteins to permit compensation for the nonspecific binding of antibodies via physical or electrostatic interaction. For example, bacteriophage expressing irrelevant peptides, or no inserted peptides, can be employed as negative control antigens. Where the polypeptide marker antigens are employed as purified peptides, irrelevant peptides are suitable negative controls.

In an antibody binding assay employing an array of polypeptide marker antigens and control antigens, the array is preferably blocked to minimize nonspecific binding of antibodies. The array is then exposed to a body fluid, preferably serum, of a patient being assessed for risk of cancer recurrence. Although serum is preferred, any body fluid known in the art to contain antibodies can be employed, for example plasma, blood, saliva, tears, and spinal fluid. Replicate arrays are exposed to suitable control sera. Negative control sera can comprise the sera of normal single or pooled individuals, single or pooled patients who did not experience recurrence, or mixtures of normal and nonrecurrent sera, with the sera being selected and prepared by means well-known in the art. Positive control sera can include sera from patients undergoing OVCA recurrence. Preferably, sera from multiple OVCA patients is pooled, and the pool is verified to include a positive signal for each polypeptide marker antigen, that is, an autoantibody that binds to each polypeptide marker antigen employed in the array. Alternatively, positive control human monoclonal antibodies can be developed from OVCA patient B cells or from immunoglobulin libraries developed from those cells. Screening of clones of hybridomas or other expressing cell types can be accomplished by assay of the binding of secreted antibodies to the polypeptide markers of the present invention. This approach has the advantage of providing a consistent and limitless supply of positive control antibodies.

Once serum autoantibody biomarkers have been allowed to bind to the marker antigens, the arrays are washed and the presence of specifically bound antibody is indicated and quantitated by means of a signal generating system.

Preferably, the signal generating system is a dual fluorescence system. A typical suitable system includes, a biomarker-binding antibody, that is, an antibody recognizing an autoantibody biomarker that has been bound by a polypeptide marker antigen. The dual fluorescence system also includes a normalization reagent that recognizes a nonantibody binding moiety of the polypeptide marker antigen, for example a constant capsid protein of a phage particle displaying the marker antigen. The signal produced by the normalization reagent permits the correction of the autoantibody biomarker binding results for the amount of marker antigen available to bind the autoantibody biomarker. The biomarker-binding antibody is coupled directly or indirectly to a first fluorescence label, and the normalizing reagent is coupled directly or indirectly to a second fluorescence label. In an exemplary phage display detection system, an anti-human immunoglobulin (Ig) antibody coupled to the fluorescent dye Cy5 produces a red fluorescence signal that is used to quantitate an autoantibody biomarker bound to a marker antigen. An anti-phage capsid antibody coupled to Cy3 produces a green fluorescence signal that is used to normalize the red fluorescence according to the quantity of display phage capsids present in the assay. Coupling of the antibodies to fluorescent dyes can be accomplished by chemical conjugation or by use of a labeled secondary antibody. Antigen binding assays according to the present invention can also be performed with a only a biomarker-binding antibody or other biomarker-binding reagent, without normalization.

An exemplary assay for the binding of serum antibodies to phage-displayed peptide antigens is disclosed in the publication by Chatterjee et al. (17). Briefly, phage clones displaying polypeptide antigens are amplified in E. coli and prepared as bacterial lysates by well-known techniques such as those described in Novagen T7 Select® Manual, User Protocol TB178 Rev. D 0311JN. Phage lysates at suitable titers, are spotted in quintuplicate onto FAST slides (Schleicher & Schuell, Keene, N.H.) by a robotic microarrayer, Prosys5510TL (Cartesian, Inc., Ann Arbor, Mich.). T7 monoclonal antibody (Novagen) and goat anti-human IgG (Pierce) are labeled with monofunctional NHS ester-activated Cy3 and Cy5 dyes, respectively, following the manufacturer's instructions (Amersham Biosciences Corp., Piscataway, N.J.). Human serum to be assayed can contain anti-E. coli antibodies which can react with traces of E. coli proteins in the phage lysate. In order to block anti-E. coli antibodies, serum samples are preferably pretreated with 150 µg of bacterial extract for 1 h at room temperature The slides are blocked in 4% milk/PBS/0.1% Tween 20 for 1 hour at room temperature and incubated with human serum at a dilution of 1:300 in PBS at room temperature for 1 hour. The slides are rinsed in PBS and washed thrice in PBS/0.1% Tween 20 for 10 minutes each at room temperature and then incubated with Cy3-labeled-T7 anti-capsid antibody at a dilution of 1:70,000 and anti-human IgG labeled with Cy5 at a dilution of 1:3,000 in PBS for 1 hour in the dark. The slides are washed thrice in PBS/0.1% Tween 20 for 2 minutes each and then twice in PBS for 2 minutes each and air dried. The slides are scanned in an Axon Laboratories 4100A scanner (Palo Alto, Calif.) using 532 and 635 nm lasers. The ratio of anti-T7 capsid and antihuman IgG is determined by comparing the fluorescence intensities in the Cy3- and Cy5-specific channels at each spot using ImaGene software (Biodiscovery, Inc., El Segundo, Calif.)

Alternatively, any suitable signal generating system known in the art can be employed to detect and quantitate the binding of an autoantibody biomarker to a marker antigen, with the signal generating system including at least one label component which generates a detectable signal relating to the amount of antibody bound to a marker antigen. The label can be any molecule that produces or can be induced to produce a signal, such as a fluorophore, an enzyme, a chemiluminescent molecule, or a photosensitizer. Thus, the signal is detected and/or measured by detecting fluorescence, enzyme activity, luminescence, or light absorbance. Suitable labels include, by way of illustration and not limitation, enzymes such as alkaline phosphatase, glucose-6-phosphate dehydrogenase ("G6PDH") and horseradish peroxidase; ribozyme; a substrate for a replicase such as Q-beta replicase; promoters; dyes; fluorescers such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; photosensitizers; particles such as latex or carbon particles; suspendable particles; metal sol; crystallite; liposomes; cells, etc., which can be further labeled with a dye, catalyst, or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescent or chemiluminescent molecules are disclosed in Litman, et al., U.S. Pat. No. 4,275,149, at columns 30 and 31; which are incorporated herein by reference.

The signals produced by the binding of autoantibody biomarkers to the isolated polypeptide marker antigens and controls are analyzed with a signal analysis system to determine the amount of autoantibody biomarker that has bound specifically to each marker antigen, especially with regard to whether the binding is higher than nonspecific background binding. The results can, for example, be in the form of absolute or relative fluorescence values, or in the form of amounts of bound antibody as determined according to a standard curve. Preferably, the analysis is automated. Exemplary automated signal analysis devices and analysis software packages include, but are not limited to the Odyssey® imaging system (LI-COR Biosciences, Lincoln, Nebr.), and the previously mentioned Axon Laboratories 4100A scanner, both of which can be employed in conjunction with ImaGene™ software (Biodiscovery, Inc., El Segundo, Calif.).

The results of the antibody binding assay are preferably interpreted by comparing fluorescence or other signal values to calibration curves of signal values obtained by exposure of the marker antigens to standard control sera. Sera from normal individuals, recurrent OVCA patients, and nonrecurrent OVCA patients, preferably in the form of pooled sera from multiple individuals, are appropriate standards for the calibration of assays of serum autoantibodies predictive of recurrence. The standards are used to construct standard calibration curves by methods well-known in the art. Example protocols for the use of such standards are readily available in reference (55).

An exemplary phage display system for the expression of the isolated polypeptide marker antigens of the present invention is the T7 isocahedral phage display system, as described in Example 1 and in U.S. Pat. No. 7,964,536. The present invention is not limited to the T7 system. Any phage display system that can express polypeptides can alternatively be used, including other isocahedral phages such as T4, and filamentous phages such as M13, fd, and fl (56). In Example 1, the autoantibody biomarkers detected are of the human IgG class, but there is no indication that autoantibodies indicative of OVCA recurrence risk should be limited to that Ig class or to human cases. The T7 and other phage display systems are capable of displaying antigens that specifically bind particular paratopes of IgA, IgE, and IgM antibodies, in both human and nonhuman systems (57-59).

The isolated polypeptide marker antigens of the present invention enable a user to determine whether an OVCA patient is at risk of disease recurrence after a first line ovarian cancer treatment. It is likely that patients determined to be at risk of recurrence by the present invention are already undergoing recurrence in the form of subclinical tumor. It is also possible that no recurrence has yet occurred, and that one or marker antigens of the present invention is detecting an autoantibody biomarker induced by a risk-associated antigen of the original tumor. A method according to the present invention includes the steps of collecting a sample of a body fluid from an ovarian cancer patient; exposing the sample of a body fluid to one or more polypeptide marker antigens selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10; quantitating the specific binding of an autoantibody biomarker by the polypeptide marker antigen; detecting the presence of the autoantibody biomarker in the sample of body fluid; and determining that the ovarian cancer patient is at risk of ovarian cancer recurrence. The preferred body fluid is serum, and collection can be made following a first-line treatment or a later course of treatment; during a course of treatment; or prior to any treatment.

When patients are determined to be undergoing recurrence, the present invention includes a method of treatment of recurrence directed selectively to the patients at risk. The method includes the administration of treatment in addition to, or instead of, the appropriate first-line therapy for these patients. One mode of additional treatment is the initiation of second-line ovarian cancer therapy. Second-line therapies are well known in the art. They include, but are not limited to, combinations of platinum and taxanes. If the disease has become refractory, second line therapies can include topotecan, gemcitabine, paclitaxel, inhibitors of vascular endothelial growth factor (VEGF) such as bevacizumab, epidermal growth factor receptor (EGFR) inhibitors such as erlotinib, and poly(adenosine diphosphateribose) polymerase (PARP) inhibitors. (60) In cases in which more than two courses of treatment are possible, the terms "first-line" and "second-line" can be used in a relative sense, with the terms "first-line" denoting an earlier treatment and "second-line" denoting any treatment following the earlier treatment. Other possible treatments for recurrent OVCA include prolonging first-line treatment beyond its initially planned course, and initiating maintenance treatments according to appropriate maintenance protocols current in the art.

The method of the present invention is not limited to assessing risk of recurrence during a period following completion of first-line treatment, and in patients who have responded to that treatment. The method can also be employed while first-line treatment is still in progress, and can be applied to patients not necessarily showing a response to that treatment.

The isolated polypeptide markers of the present invention equip a clinician with a new tool for directing second-line OVCA treatment to the patients who are most at risk of recurrence, and who stand to benefit the most from the treatment, while withholding treatment, and its attendant side effects, from patients who would not benefit from it. A final decision as to whether further treatment should be initiated is of course made by a clinician on the basis of many factors, such as treatment history, the side effects of further treatments, and the health and level of function of the patient. The polypeptide marker antigens and methods of the present invention provide a clinician with an important new factor to consider in making the final decision.

Also included in the present invention is a method for isolating antibodies for the detection and targeting of OVCA on the basis of their affinities to the isolated polypeptide marker antigens of the present invention. The present invention also includes the detecting and targeting antibodies isolated by this method. It is likely that the autoantibody biomarkers detected by the polypeptide marker antigens of the present invention were originally induced by epitopes of ovarian tumor or of tumor-associated tissue such as abnormal stroma, It is therefore likely that antibodies that bind specifically to the polypeptide marker antigens will also bind specifically to tumor or tumor associated tissue in vivo or in vitro. For example, a series of monoclonal antibodies can be screened against the polypeptide marker antigens of the present invention. Antibodies specifically reactive to one or more of the polypeptide marker antigens can be identified by well known hybridoma screening methods such as those described in reference (61), pp 174-195. The hybridomas that produced the reactive monoclonal antibodies can then be isolated and use in the production of ovarian cancer detecting and targeting antibodies. In another example, an affinity column or other affinity medium can incorporate the polypeptide marker antigens of the present invention. The column can be exposed to a pool of mixed antibodies, and washed to remove nonbinding and nonspecifically bound antibodies. Specifically bound antibodies can be eluted and identified as ovarian cancer detecting and targeting antibodies. It will be understood that these examples are not limiting, and that the polypeptide marker antigens of the present invention can be used with many other antibody screening methods. Such methods are readily selected and employed by those skilled in the art, from references such as reference (61), pp. 421-467 and 511-552. The antibodies isolated by means of the present invention can be modified to include labels, immunostimulants, and toxic moieties, or can have direct toxic effects, for example by triggering apoptosis or blocking stimulatory receptors.

Example 1: Detection of Tumor Autoantibody Biomarkers for Predicting Ovarian Cancer Recurrence Materials and Methods Study Population.

Patients diagnosed and treated for late stage serous OVCA at Karmanos Cancer Institute or St. John Hospital & Medical Center (Detroit, Mich.) or Oakwood Hospital & Medical Center (Dearborn, Mich.) were entered onto the study at the time of their diagnosis or during a return visit within 5 years of initial diagnosis. Medical records were reviewed to determine CA125 levels, disease status, chemotherapy status, and time to recurrence (TTR) over a multi-year period. Cases were limited to those diagnosed between 1997 and 2007 to ensure sufficient follow up. On the basis of this information patients were divided into two groups: 1) No Recurrence (NR), defined as no clinical evidence of disease for at least 48 months, and 2) Recurrent Disease (R), defined as clinical evidence of disease and/or doubling of CA125 within approximately 3 years of diagnosis (range 11-39 months). Recurrent disease patients selected for the validation set had a disease-free interval of at least six months (range 6.6-34).

Serum Sample Collection and Processing.

Serum was collected and processed described in a previous study (17. Serum samples were selected for use on the basis of time since diagnosis, CA125 level, disease status, and chemotherapy status at the time of blood collection. For the initial study specimens from three time points were used for all cases (R and NR); the specimen obtained at time of enrollment and at two post-diagnosis intervals, which are given for each patient.

For the validation study, serum samples were collected from recurrent cases at a median time of 9.07 months (range=2.1 to 18.9 months) prior to clinical recurrence. Most patients had a normal CA125 and no clinical evidence of disease at that time. For nonrecurrent cases, samples were collected at least 11 months after completion of chemotherapy, with no evidence of disease and a normal CA125 level.

Study procedures were approved by the Wayne State University, St. John Hospital & Medical Center, and Oakwood Hospital & Medical Center Institutional Review Boards. All participants provided written informed consent. *Serological screening of polypeptide antigen arrays.* Peptide arrays were prepared by amplifying 174 individual antigen-expressing T7 phage clones (initial study) and 56 individual antigen-expressing T7 phage clones (validation study), and arraying their lysates onto a nitrocellulose membrane using the Beckman Biomek 2000® liquid handling robot. This robot, equipped with a 96-pin printing head, spotted the bacteriophage samples contained in 96 well plates onto nitrocellulose membranes in a 4×4 pattern. Empty phage vectors were used as negative controls in both the initial and validation studies. The nitrocellulose membranes were blocked with 5% dry milk for 1 h at room temperature. For the initial serological screening, the blocked nitrocellulose membranes (arrays) were processed with serum samples that were obtained from recurrent (n=5) and non-recurrent (n=5) OVCA patients. For the validation study, the blocked membranes were processed with samples from the initial study (see above) along with serum samples obtained from independent cohorts comprised of recurrent (n=25) and non-recurrent (n=5) OVCA patients. In order to block anti-*E. coli* antibodies, serum samples were pretreated with 150 µg of bacterial extract for 1 h at room temperature. For the initial antigen selection serological study and the validation study, 1:100 serum dilution was used. The membranes were washed three times with 0.24% Tris, 0.8% NaCl, 1% Tween-20 (TBST) for 10 min each and incubated with rabbit-anti human secondary antibody conjugated with IR-Dye800 (Rockland, Gilbertville, Pa., USA) at 1:5000 dilution for 1 h at room temperature. The membranes were then washed three times with TBST for 10 min each, and two times with 1×PBS for 5 min each. The arrays were scanned using an Odyssey® imaging system at 800 nm wavelength according to manufacturer's instructions. The fluorescence intensity at each spot was quantified using ImaGene™ software (Biodiscovery, Inc., El Segundo, Calif.). Nitrocellulose membranes (3 membranes for the initial study; 12 membranes for the validation study) were separately treated with mouse anti-T7 antibody directed toward T7 phage coat protein (EMD Bioscience Inc: Novagen, San Diego, Calif., USA), exactly following the above procedure. Alexa Fluor 680 Goat anti-mouse IgG secondary antibody (Molecular Probes, Invitrogen, Grand Island, N.Y., USA) at 1:10000 dilution was used and the membranes were scanned using Odyssey® imaging system at a wavelength of 700. The quantified images were used for data normalization.

Statistical Analyses

1) Background Correction and Normalization.

The following procedure was followed for both the initial and the validation study. The image quantified files were read into R using the Limma package suite of software. Any measurement with a "0" weight (defined as an empty or poor spot) was set to "missing". Each of the immunoassays (initial and validation study) was background corrected using the "minimum" method. That is, the background intensities were subtracted from the foreground intensities for each color channel [red (R) and green (G)]. Any resultant intensity that was zero or negative after the subtraction was set to half of the minimum of the positive corrected intensities from that channel. This created the signal intensity measurement for each assay. A normalization channel array was created using the point-wise median of the 1536 intensity values from the three assays (for initial study) and 12 assays (for validation study) performed with only with the anti-T7-capsid antibodies. Then each assay was normalized to this channel assay using the "median" method. That is, the log base 2 intensity ratio $M=\log(R/G)$ was computed for each assay. Then the median (M) was subtracted from all M values within the assay. Subsequently for each of the assays, the median corrected intensity measurement for each of the antigens was calculated, with each measure performed in triplicate on each assay. This dataset was used to conduct all of the analyses that are described in the Results section.

ii) Statistical Analyses for the Initial Study.

As this screening dataset had only 10 patients (5 recurrent, 5 non-recurrent), many different statistical methods were used to derive a list of polypeptide marker antigens to analyze in the set of patients in the validation experiment. The statistical methods used included t-tests and the Wilcoxon rank sum test (non-parametric analog to the t-test). Marker antigens that were significant at 0.05 for any of the three tests were retained for the validation study.

iii) Statistical Analyses for the Validation Study.

(a) CART.

Classification and Regression Trees (CART) is a form of binary recursive partitioning. The term "binary" implies that each group of patients, represented by a "node" in a decision tree, can be split into 2 child nodes and the partitioning process can be repeated many times. CART identifies subset of the predictor (independent) variable(s) based on exhaustive search of all possibilities that best associate with the response variable. CART bootstrapped analysis was used in biomarker analysis to determine the significance of each measured antigen. A CART analysis was constructed on a bootstrapped training (or model building) dataset to identify thresholds for each antigen predicting cancer recurrence status. Next, the model was applied to a test dataset with no overlap of patients from the training dataset to determine if the antigens threshold model was predictive in a new dataset. This process was repeated many times. The 10 patients that were measured for the initial study were also measured in the validation study to validate the reproducibility of the marker antigen measurements in addition to the 30 new patient samples (25 recurrent, 5 non-recurrent). As the recurrent and non-recurrent sample sizes were quite different, weighted analyses were performed for the validation study. The nominal level of significance was determined using logistic regression, t-tests and Wilcoxon rank sum tests for each antigen for the 30 new patient samples.

Bootstrapping was then used in conjunction with both logistic regression and classification and regression trees (CART) to evaluate if any of the polypeptide antigens were predictive of recurrence status. Briefly, a bootstrapped sample of 40 patients was created (ensuring that the 10 patients that were measured in the initial study were always in the training dataset). A prediction model was created (either a single antigen logistic regression or CART model) using the bootstrapped sample. The model was then applied to the holdout patient samples (not in the bootstrapped sample) and retained the predictive probability of recurrence. Over 10,000 bootstrapped samples, each of the new 30 patient samples was held out approximately 46% of the time. The predicted values for each polypeptide antigen were summarized for the pooled recurrent cases using the median and inter-quartile range (IQR). A similar summarization was done for the non-recurrent patients. Those polypeptide antigens for which the IQR was greater than 0.5 for the recurrent cases and less than 0.5 for the non-recurrent cases were deemed significant. Using the IQR instead of a confidence interval is necessary since individual patients may be poorly predicted; the IQR will yield polypeptide marker antigens that predict well over all samples. Individual plots of the 95% bootstrapped predicted confidence intervals were produced to determine which patients were poorly predicted by the model.

A CART model was also constructed for these selected antigens based on the test set of 30 samples. The results, in Table 1, demonstrate the results of the CART-selected threshold used as a predictor of recurrence status.

(b) Logistic Regression.

Logistic regression is a statistical method for modeling a binary endpoint (yes/no, recurrent/non-recurrent). In this model the response variable has only 2 values, typically denoted as 1 or 0. In a study of whether a patient recurs (y=1) or does not recur (y=0) after the front-line treatments, the probability of an event occurring is related to the predictor variable through the logit link function: $\log(p/(1-p))$; where p is the probability of recurrence. The exact statistical formulation of the model is $\log(p/1-p)=\beta 0+\beta 1x$, where p is the probability of recurrence and x is the predictor variable.

In this study, using logistic regression, the reactivity of each polypeptide antigen from the learning dataset was used as the predictor variable to predict recurrence status. Similarly as described in the CART analysis, a logistic regression model for each antigen was then constructed on a bootstrapped sample of patient sample. The corresponding test data set was used as the model validation data set.

Results

The goal of this study was development of autoantibodies directed against TAAs as a potential prediction tool for detecting OVCA recurrence at an early time that could improve a clinician's ability to reimplement chemotherapy for a patient.

In an initial study, 174 polypeptide antigens known to bind serum autoantibodies of OVCA patients were tested for their ability to discriminate five recurrent OVCA patients from five nonrecurrent patients. Fifty-six of the polypeptide antigens showed significant discrimination as determined by statistical analyses including t-tests and the Wilcoxon rank sum test. This panel of 56 polypeptide antigens was entered into a validation study wherein they were tested on an expanded sample of OVCA patients and analyzed for ability to predict recurrence, that is to serve as marker antigens, by both CART and logistic regression analysis. In the validation study, the utility of the panel of 56 polypeptide antigens was compared to that of CA125 for predicting OVCA recurrence at a median time of 9.07 months (range=2.1 to 18.9 months) in a population where majority of patients showed recurrence without a rise in CA125 level.

Validation of Polypeptide Marker Antigens Biomarkers for Detection of Autoantibodies Associated with OVCA Recurrence at an Early Phase.

Serological immunoscreening of protein arrays was performed with serum obtained from an independent cohort of recurrent (n=25) and non-recurrent (n=5) OVCA patients as well as with serum samples used for the initial study. All the samples that were used for the initial study of antigen selection were only included in the training model and not used in the testing set during the validation process.

Figure 1B:
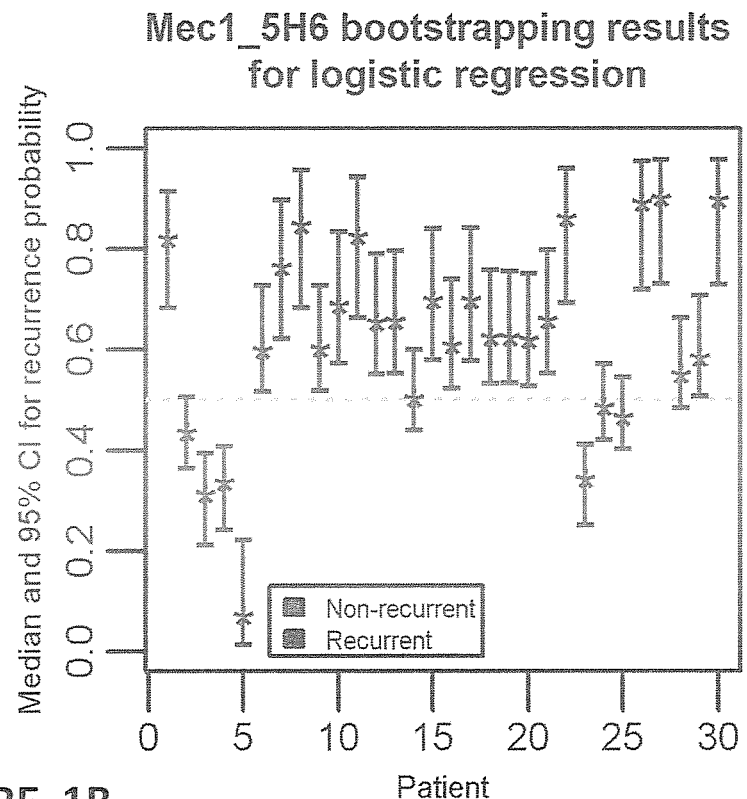
FIG. 1B shows a determination of median and 95% confidence interval of the predicted probability of recurrence of each ovarian cancer patient, based on the performance of polypeptide marker antigen Mec1_5H6, using logistic regression bootstrapped algorithm.
Figure 1C:
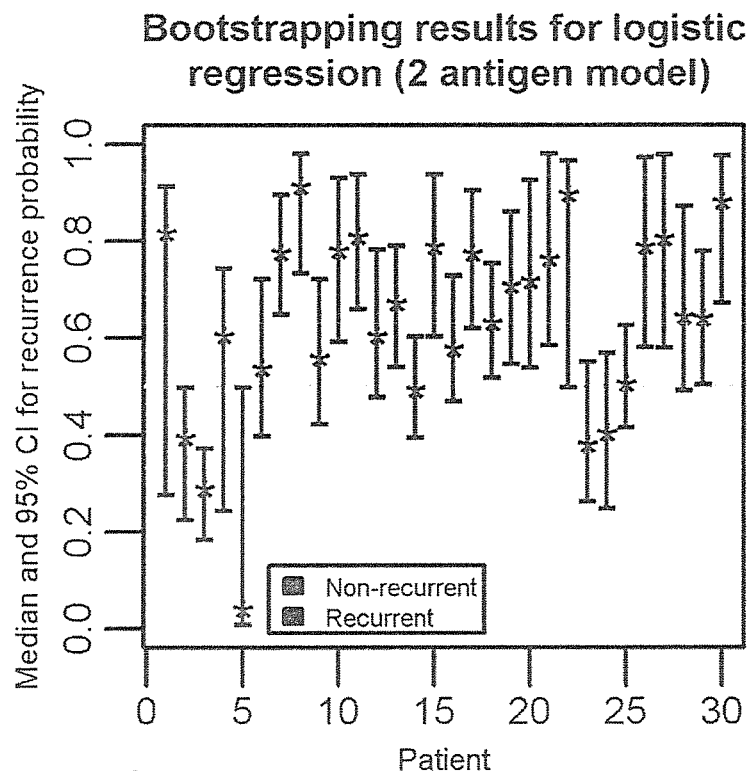
FIG. 1C shows a determination of median and 95% confidence interval of the predicted probability of recurrence of each ovarian cancer patient, based on the performance of the polypeptide marker antigens Mec1_4B7 and Mec1_5H6 in combination, using logistic regression bootstrapped algorithm.
Figure 2:
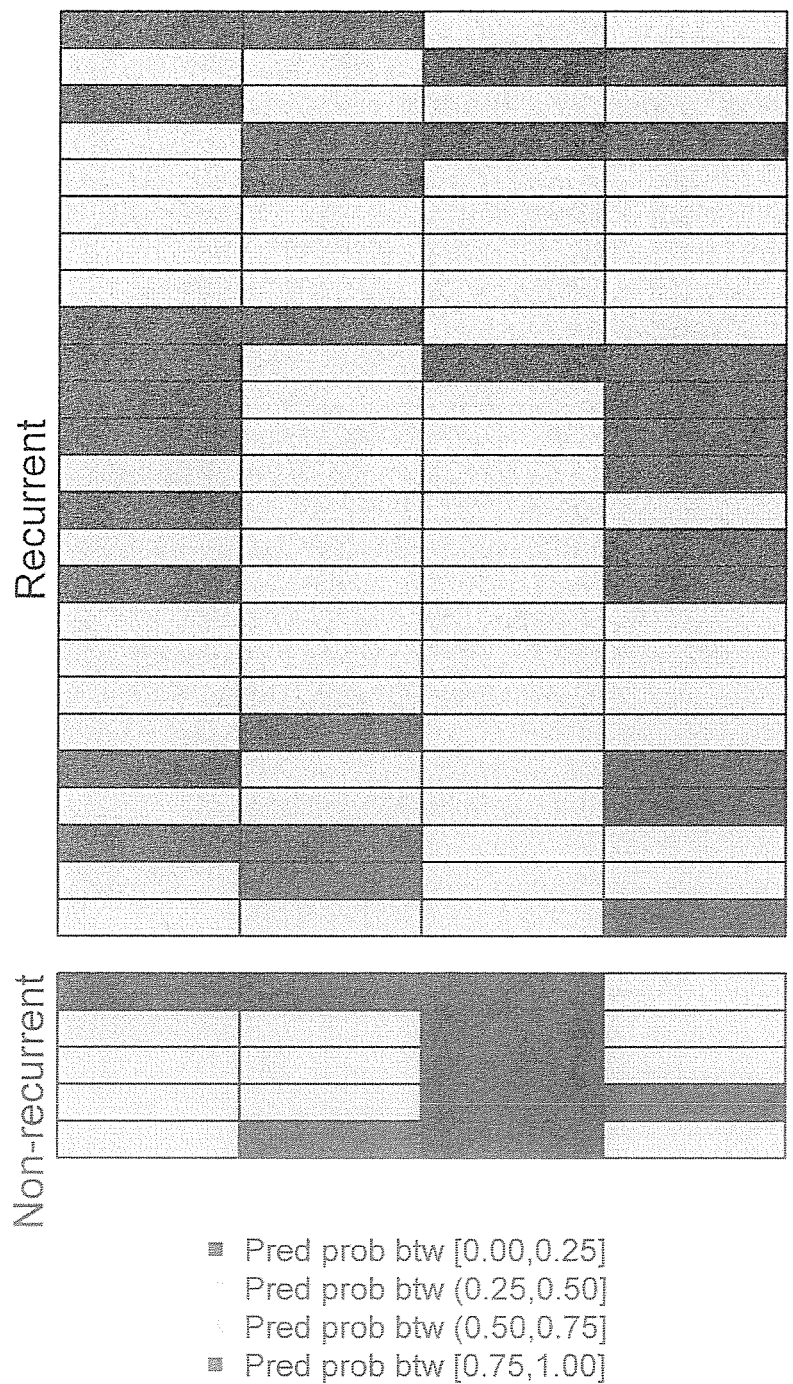
FIG. 2 shows a representation of predicted probability of recurrence of ovarian cancer patients based on the performance of each polypeptide marker antigen derived from bootstrapped samples, with the predicted probabilities for Mec1_4B7 and Mec1_5H6 computed as the median predicted value from the "testing set" from 10,000 bootstrapped logistic regression analyses (which always included the 10 samples previously used in the training set), and with predicted probabilities for Mec1_4H4 and p53 computed as the median predicted value from the "testing set" from 10,000 bootstrapped CART analyses (which always included the 10 samples previously used in the training set)

Using weighted logistic regression on the 30 newly measured patient samples, 28 polypeptide antigens proved statistically significant (p≤50.05) with respect to predicting recurrence status. Two of those antigens (Mec1_4B7, Mec1_5H6) were statistically significant using the boot-strapped algorithm. The median and pooled IQR values for Mec1_4B7 antigen were 0.695 (0.541, 0.817) and 0.322 (0.237, 0.399), and for Mec1_5H6 antigen were 0.652 (0.568, 0.774) and 0.352 (0.271, 0.456) for recurrent and non-recurrent cases respectively. The median and 95% confidence interval of the predicted probability of recurrence for each patient sample are shown in the FIGS. 1A and 1B. Only a few samples out of 30 for each antigen were poorly predicted. A rule of Mec1_4H4 or Mec1_4B7 would be accurate for all but 1 non-recurrent patient. A rule of Mec1_4H4 or Mec1_5H6 would be accurate for all but 1 non-recurrent patient (a different patient) (FIG. 2). Combining these polypeptide antigens in a single logistic regression model does not improve prediction (FIG. 1C).

Figure 1D:
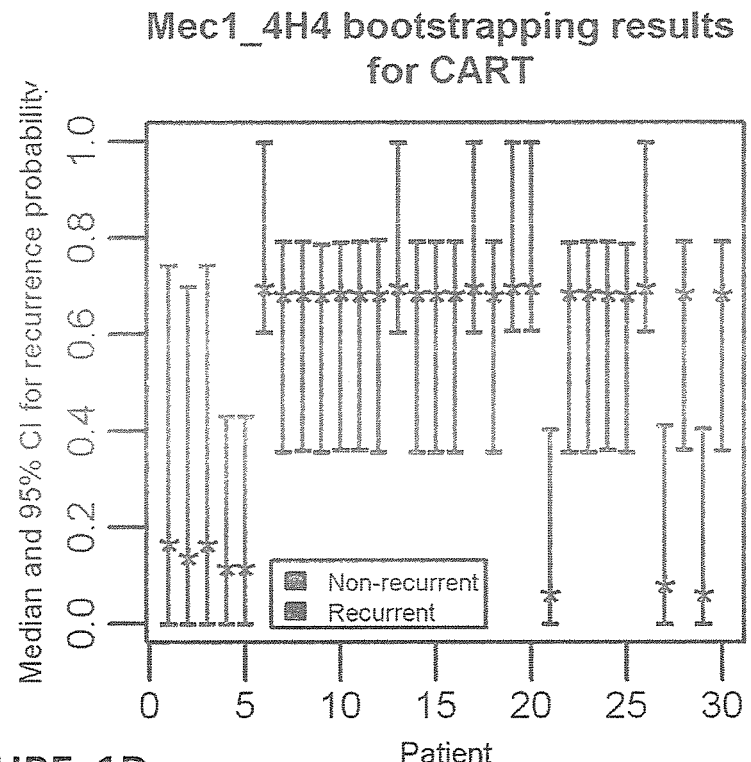
FIG. 1D shows a determination of median and 95% confidence interval of the predicted probability of recurrence of each ovarian cancer patient, based on the performance of the polypeptide marker antigen Mec1_4H4 (D), using CART bootstrapped algorithm.

There were 10 polypeptide antigens significant at 0.05 for either a t-test or a Wilcoxon rank sum test. CART was applied to these 13 antigens to determine the optimal threshold for determination of sensitivity and specificity as shown in Table 1. One antigen, Mec1_4H4, was found to be statistically significant using the CART bootstrapped algorithm. The median and pooled IQR for this antigen were 0.682 (0.620, 0.723) and 0.138 (0.067, 0.389) for recurrent and non-recurrent cases respectively. The median and 95% confidence interval of the predicted probability of recurrence for each patient sample are shown in FIG. 1D. Note that the confidence intervals are much wider for the CART analysis than the logistic regression analysis due to the categorization involved with CART. Only 3 recurrent patient samples had incorrect median recurrence probabilities.

Figure 3:
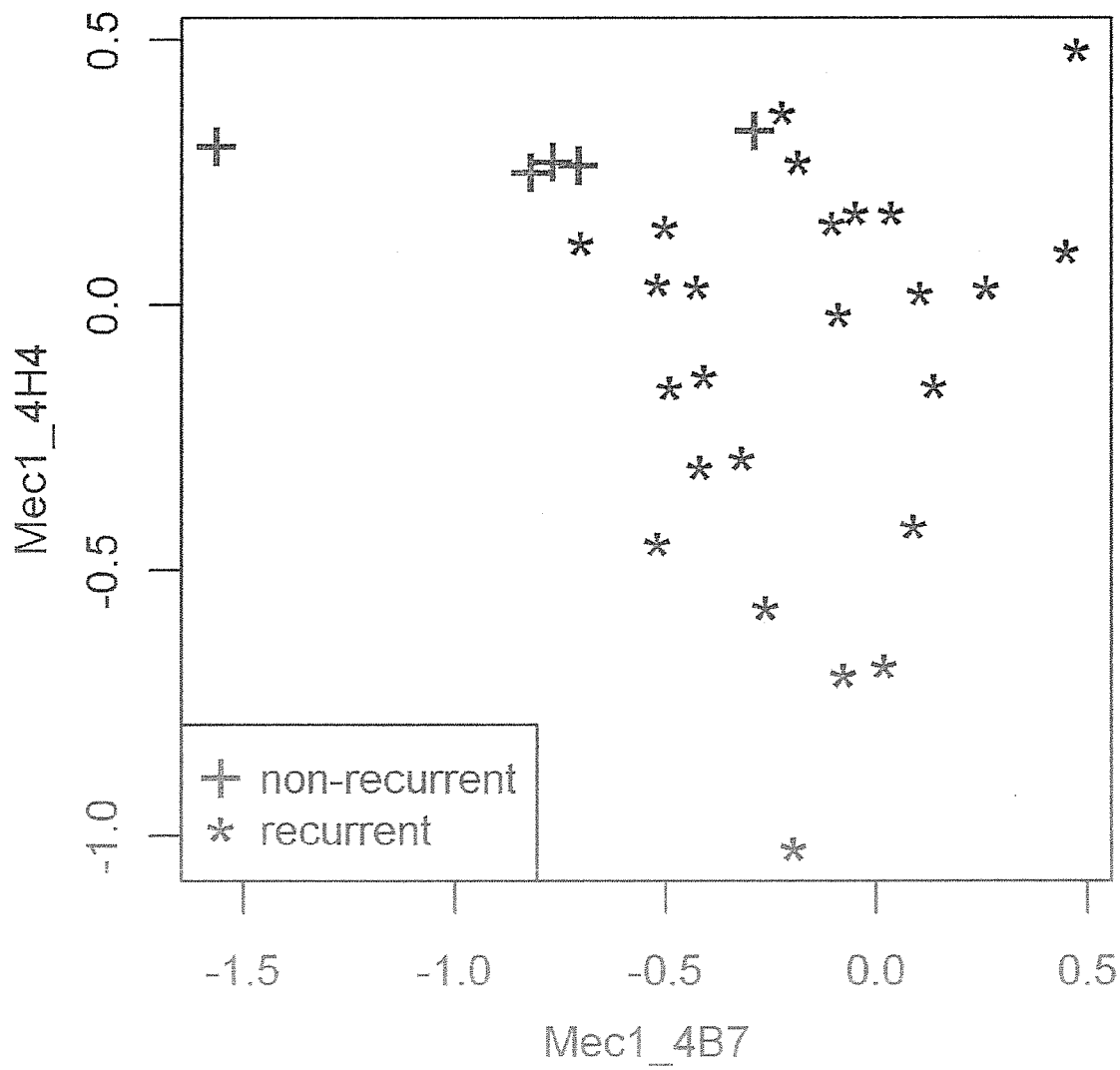
FIG. 3 shows a graphical representation of ovarian cancer validation set by recurrence status, based on correlation between 2 polypeptide marker antigens, Mec1_4B7 and Mec1_4H4.
Figure 4A:
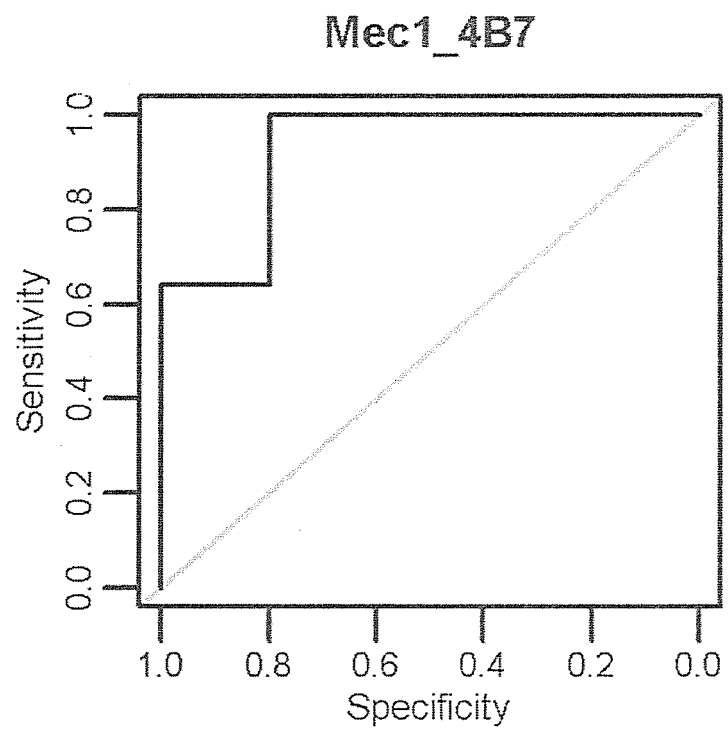
FIG. 4A shows the receiver operating characteristic (ROC) curve of the polypeptide marker antigen Mec1_4B7.
Figure 4B:
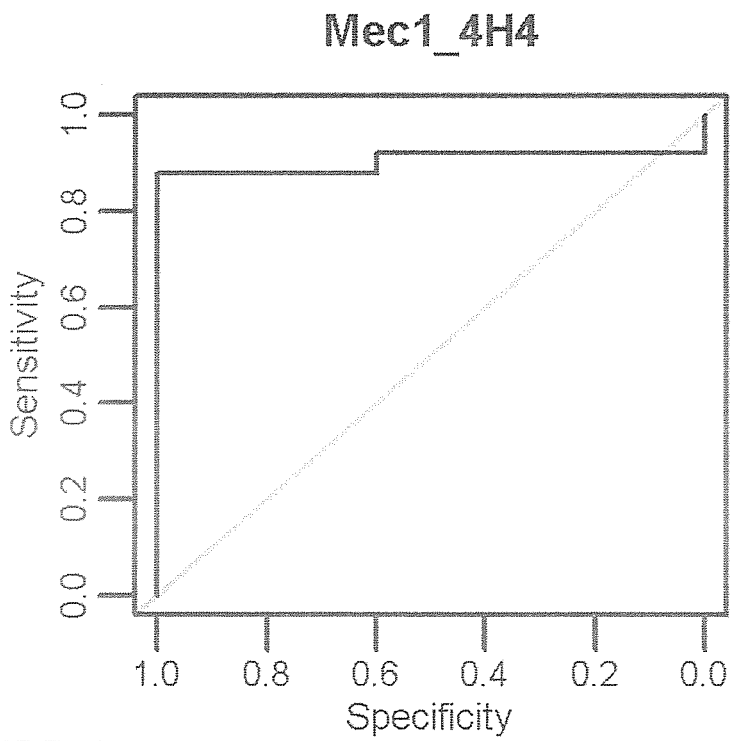
FIG. 4B shows the ROC curve of the polypeptide marker antigen Mec1_4H4.
Figure 4C:
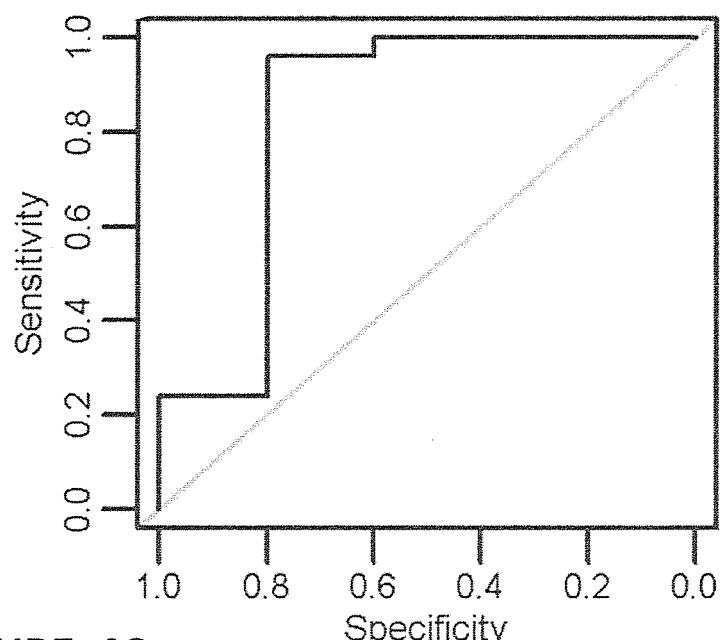
FIG. 4C shows the ROC curve of the polypeptide marker antigen Mec1_5H6.
Figure 4D:
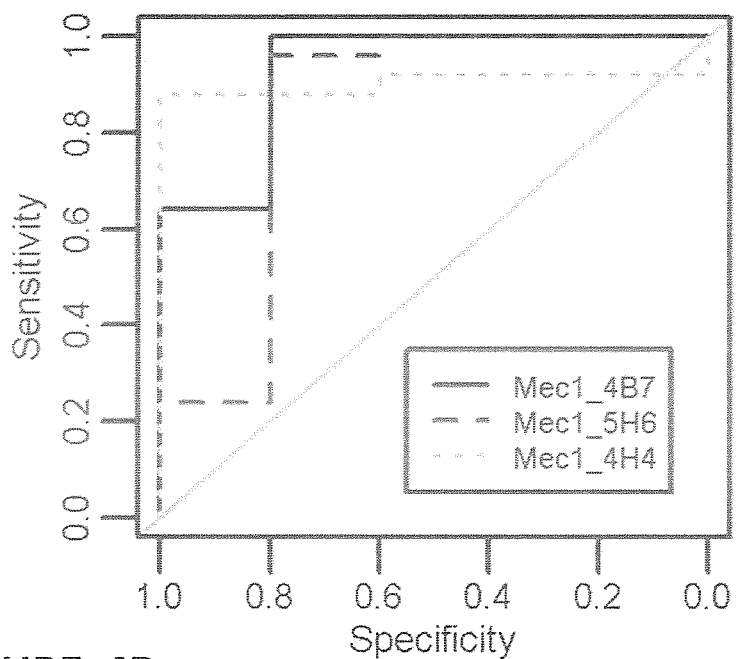
FIG. 4D shows a combination of the ROC curves of the polypeptide marker antigens Mec1_4B7, Mec1_4H4, and Mec1_5H6.

The 3 polypeptide antigens, Mec1_4B7, Mec1_4H4, and Mec1_5H6 that proved significant through either analysis were further examined. FIG. 3 shows the relationship between the 2 remaining antigens, Mec1_4B7 and Mec1_4H4 (after backwards step-wise selection on the 3 in a logistic regression model) and recurrence status of the validation samples. There is perfect non-linear discrimination between the recurrent and non-recurrent samples. The receiver operating characteristic (ROC) curves for each of the 3 polypeptide antigens are shown in FIGS. 4A-4C. The three lines are plotted on the same axis in FIG. 4D. The area under the curves (AUC) for Mec1_4B7, Mec1_4H4, and Mec1_5H6 were 0.928, 0.904 and 0.840 respectively (Table 2). The amino acid sequences of these three polypeptide antigens is given in Tables 4 and 5.

TABLE 2

The AUC values of 10 polypeptide marker antigens obtained by CART analysis

| Antigen | AUC | |
|---|---|---|
| Mec1_4B7 | (SEQ ID NO: 1)* | 0.928 |
| Mec1_4H4 | (SEQ ID NO: 2)* | 0.904 |
| Mec1_5H6 | (SEQ ID NO: 3)* | 0.840 |
| Mec1_1B4 | (SEQ ID NO: 4) | 0.792 |
| Mec1_2B3 | (SEQ ID NO: 5) | 0.792 |
| Mec1_2H1 | (SEQ ID NO: 6) | 0.776 |
| Mec1_3D5T | (SEQ ID NO: 7) | 0.832 |
| Mec1_3D7 | (SEQ ID NO: 8) | 0.872 |
| Mec1_4E8 | (SEQ ID NO: 9) | 0.744 |
| Mec1_5A3 | (SEQ ID NO: 10) | 0.896 |

Figure 4E:
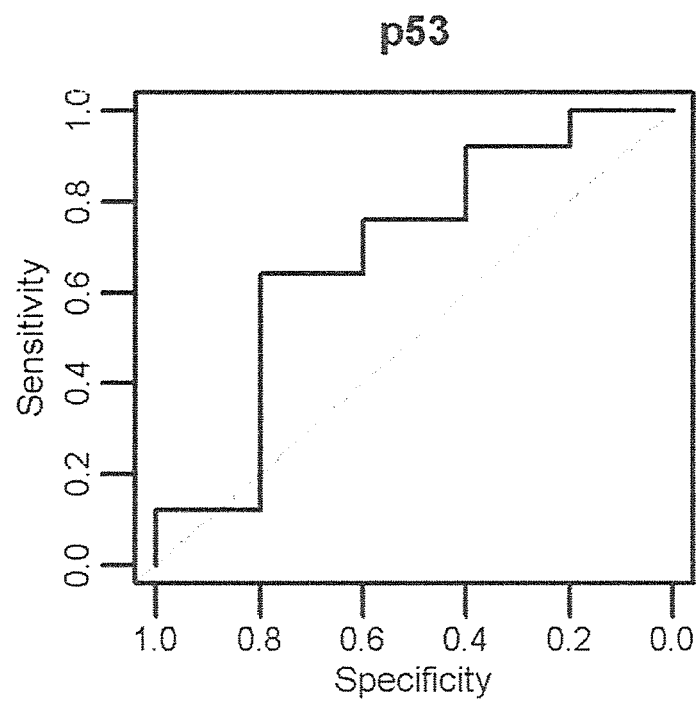
FIG. 4E shows the ROC curve of p53.
Figure 5A:
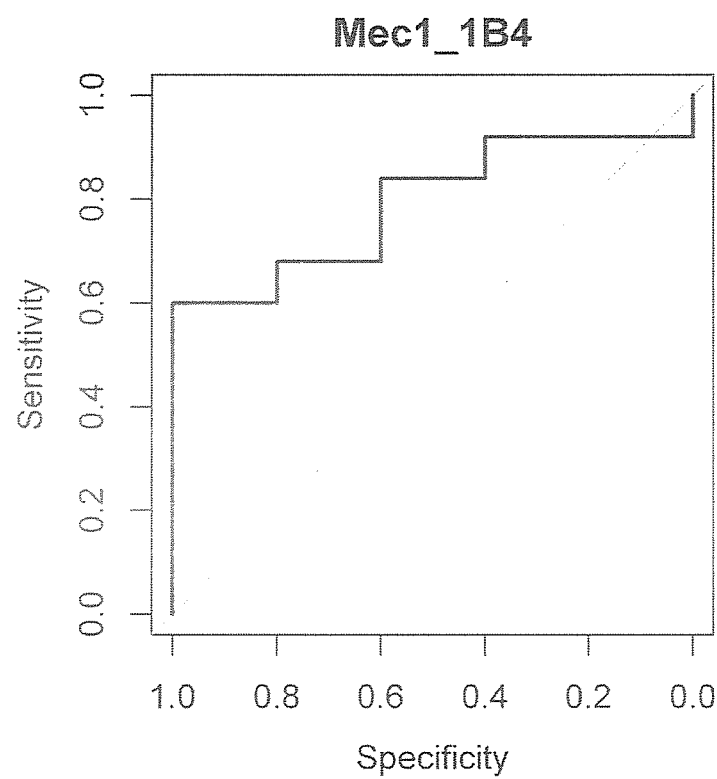
FIG. 5A shows the receiver operating characteristic (ROC) curve of the polypeptide marker antigen Mec1_1B4.
Figure 5B:
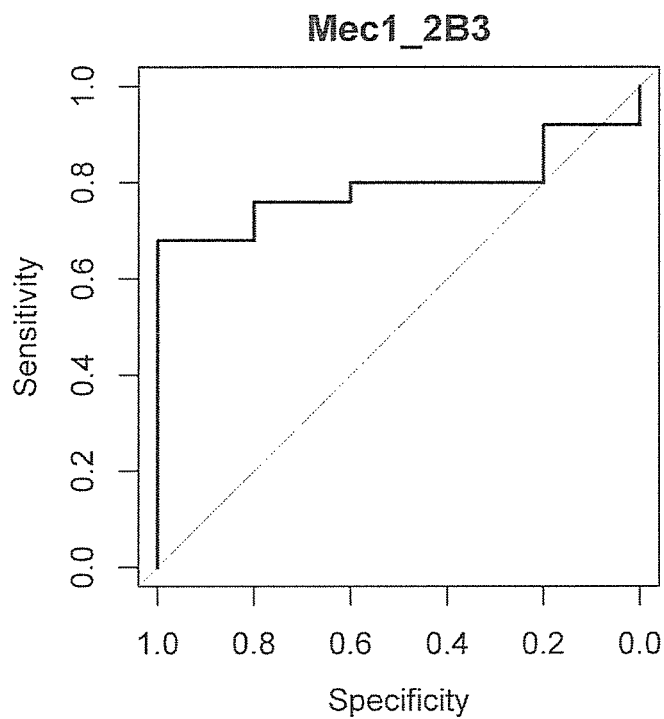
FIG. 5B shows the ROC curve of the polypeptide marker antigen Mec1_2B3.
Figure 5C:
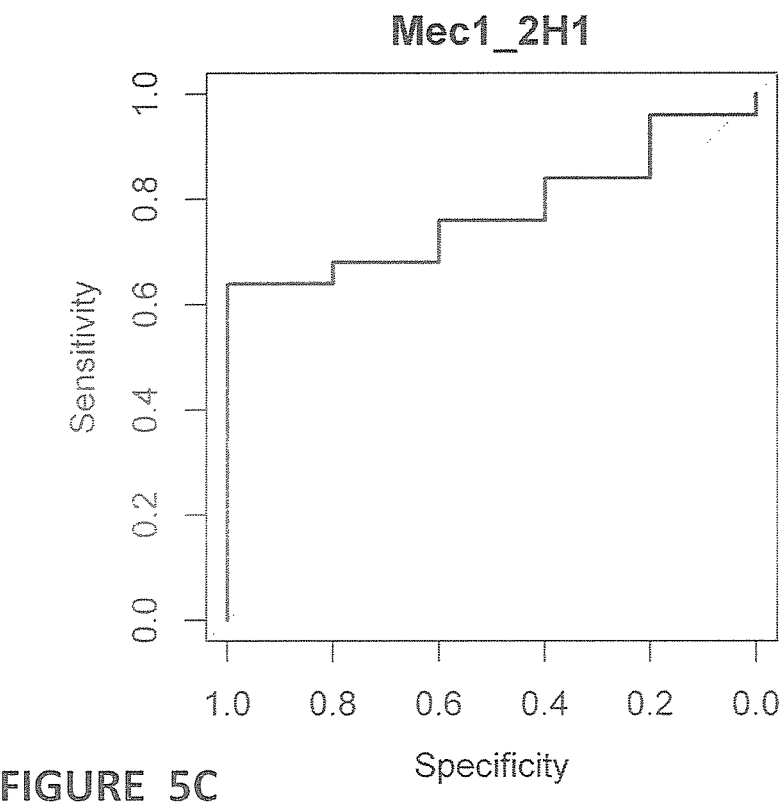
FIG. 5C shows the ROC curve of the polypeptide marker antigen Mec1_2H1.
Figure 5D:
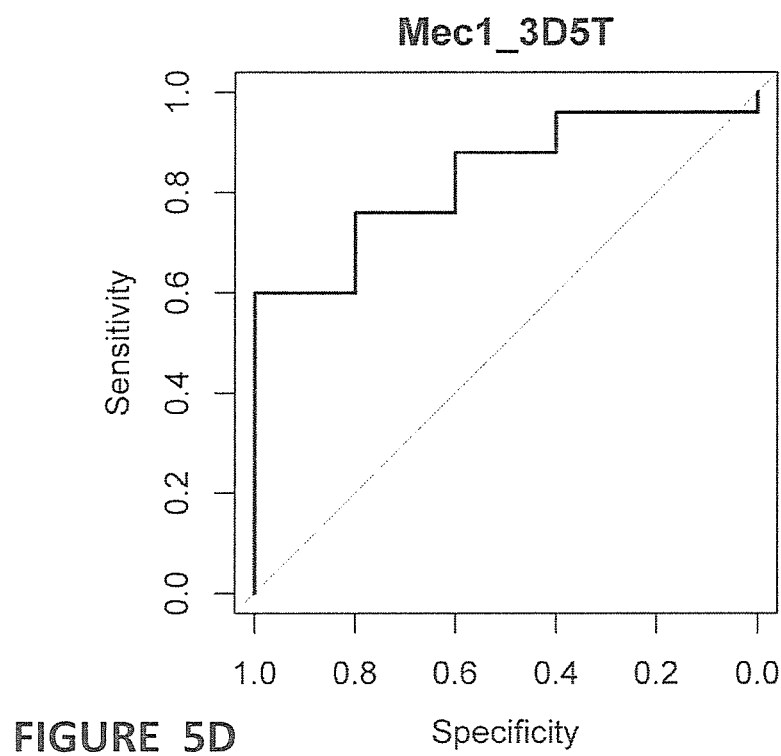
FIG. 5D shows the ROC curve of the polypeptide marker antigen Mec1_3D5T.
Figure 5E:
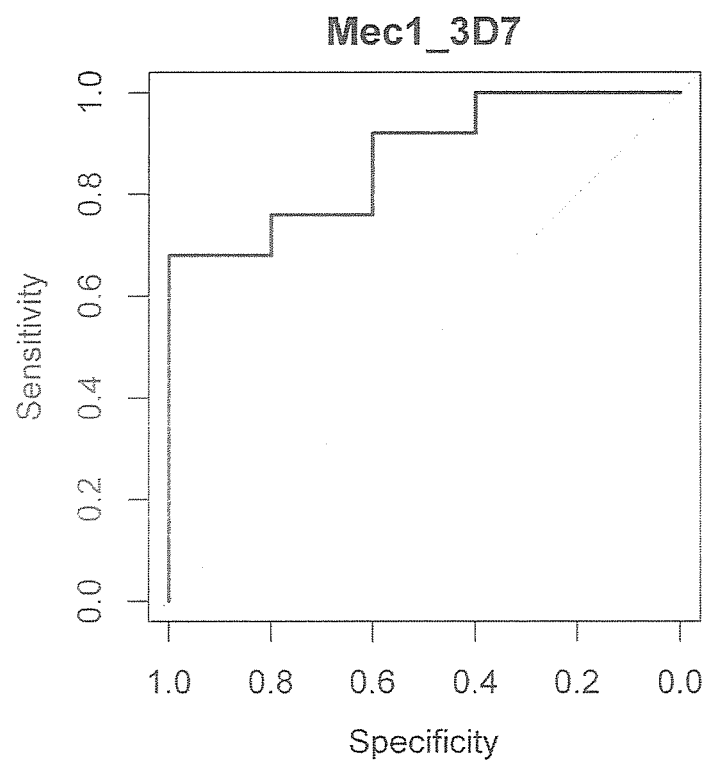
FIG. 5E shows the ROC curve of the polypeptide marker antigen Mec1_3D7.
Figure 5F:
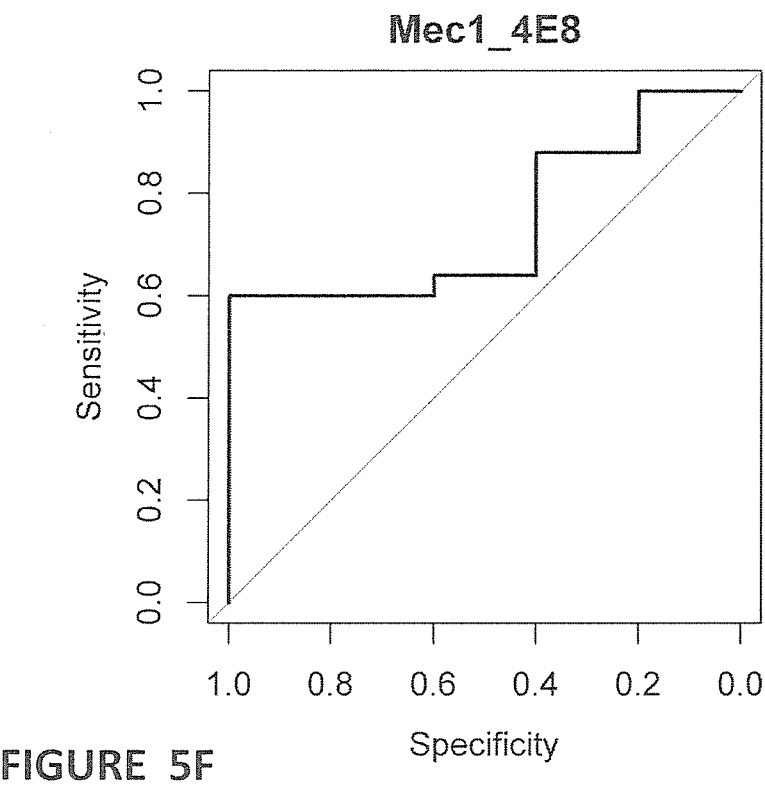
FIG. 5F shows the ROC curve of the polypeptide marker antigen Mec1_4E8.
Figure 5G:
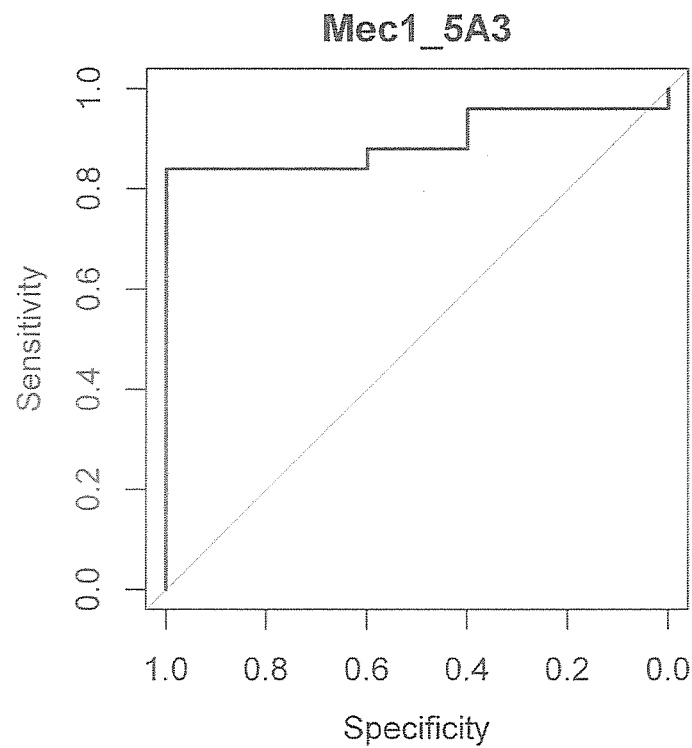
FIG. 5G shows the ROC curve of the polypeptide marker antigen Mec1_5A3.

The performance of the well-known tumor antigen p53 alone on the same sample set was poor compared to any of these 3 antigens biomarkers as indicated by its low AUC value of 0.688 (see ROC curve FIG. 4E). Because of their value in detecting autoantigen biomarkers associated with OVCA recurrence the three polypeptide antigens Mec1_4B7, Mec1_4H4, and Mec1_5H6 are included in the present invention as marker antigens.

ROC analysis indicated that seven additional polypeptide antigens are also useful predictors of OVCA recurrence; these antigens are also included in the present invention as marker antigens. These marker antigens are Mec1_1B4, Mec1_2B3, Mec1_2H1, Mec1_3D5T, Mec1_3D7, Mec1_4E8, and Mec1_5A3. Their amino acid sequences are given in Table 3. The ROC curves for each of these seven marker antigens is shown in FIGS. 5A to 5G. The area under the ROC curve (AUC) values for these seven marker antigens were found to range from 0.776-0.896 (Table 2). In

TABLE 1

The performance of 10 marker antigens obtained by CART analysis

| Antigen/threshold | TP | FN | FP | TN | Sensitivity | Specificity | PFV | NPV |
|---|---|---|---|---|---|---|---|---|
| Mec1_1B4 < 0.111 (SEQ ID NO: 4) | 15 | 10 | 0 | 5 | 60 | 100 | 100 | 33.3 |
| Mec1_2B3 >= −0.274 (SEQ ID NO: 5) | 17 | 8 | 0 | 5 | 68 | 100 | 100 | 38.5 |
| Mec1_2H1 < −0.122 (SEQ ID NO: 6) | 16 | 9 | 0 | 5 | 64 | 100 | 100 | 35.7 |
| Mec1_3D5T < 0.406 (SEQ ID NO: 7) | 15 | 10 | 0 | 5 | 60 | 100 | 100 | 33.3 |
| Mec1_3D7 >= −0.154 (SEQ ID NO: 8) | 17 | 8 | 0 | 5 | 68 | 100 | 100 | 38.5 |
| Mec1_4B7 >= −0.704 (SEQ ID NO: 1) | 25 | 0 | 1 | 4 | 100 | 80 | 96.2 | 100.0 |
| Mec1_4E8 < 0.112 (SEQ ID NO: 9) | 15 | 10 | 0 | 5 | 60 | 100 | 100 | 33.3 |
| Mec1_4H4 < 0.212 (SEQ ID NO: 2) | 22 | 3 | 0 | 5 | 88 | 100 | 100 | 62.5 |
| Mec1_5A3 >= −0.021 (SEQ ID NO: 10) | 21 | 4 | 0 | 5 | 84 | 100 | 100 | 55.6 |
| Mec1_5H6 >= −0.78 (SEQ ID NO: 3) | 24 | 1 | 1 | 4 | 96 | 80 | 96.0 | 80.0 |
| CA125 | 2 | 23 | 0 | 5 | 8 | 100 | 100 | 17.9 | contrast, the biomarker tumor antigen p53, on the same sample, whose ROC curve is shown in FIG. 4E, had an AUC value of only 0.688 (not shown). The predictive value of the seven marker antigens is further supported by their average sensitivity and accuracy values. Their average sensitivity, as calculated from the data of Table 1, is 66.3%, as opposed to a sensitivity of 8.0% for the commonly used biomarker CA125. The accuracy of the seven marker antigens, calculated from Table 2 as (TP+TN)/(TP+TN+FP+FN), is 71.9%, as opposed to 30.4% for CA125. The amino acid sequences of these seven marker antigens are given in Table 4.

In conclusion, a total of 10 polypeptide marker antigens have been proven to be useful for serological prediction of the risk of recurrence of ovarian cancer during or after primary treatment: Mec1_4B7, Mec1_4H4, Mec1_5H6, Mec1_1B4, Mec1_2B3, Mec1_2H1, Mec1_3D5T, Mec1_3D7, Mec1_4E8, and Mec1_5A3.

Discussion

The management of recurrent OVCA is a major clinical challenge because relapse after front-line chemotherapy, such as platinum-based therapy, represents an aggressive disease state which currently has no clinical biomarkers, other than p53, which has its limitations, that can indicate when to reinitiate treatment (30). The polypeptide marker antigens included in the present invention provide an early indication of recurrence in adenocarcinoma of the ovary that are sensitive to front-line chemotherapy, so that the second-line chemotherapy treatment can be implemented sooner than CA125 could detect disease for a better therapeutic outcome.

The results indicated that ten biomarker antigens were able to predict recurrence at a median time of 9.07 months prior to clinical recurrence of the disease in a population where 92% (23/25) recurrent OVCA patients had CA125 less than 35 U/ml at that time. The results also indicated that proteins known to be overexpressed in OVCA were not useful autoantigen recurrence biomarkers. In the same patient population CA125 alone detected recurrence with a low sensitivity of 8%, although all the non-recurrent OVCA patients were correctly categorized by CA125 as indicated by the high assay specificity (Table 1). The low sensitivity of CA125 was due to the enrollment of a particular group of recurrent OVCA patients for this study where the majority of patients had CA125 values below 35 U/ml at first post diagnosis interval before recurrence. It is noteworthy that of the 12 recurrent patients on whom complete longitudinal CA125 data was obtained, 11 had normal CA125 levels for an extended period prior to their recurrence (average interval 9 months, range 5.5-11.7 months). Clinical documentation of recurrence was not noted for a median of 9.07 months (range 2.1-18.9) after the appearance of biomarkers of the present invention. A limitation of this study is that few non-recurrent patients (OVCA patients who remained disease free after primary chemotherapy for greater than 4 years) were available for the validation study. Generally, monitoring of disease during or after front-line chemotherapy in OVCA patients with low CA125 levels is dependent on imaging studies that sometimes fails to detect the metastases that fall below the resolution limits of this technology. Therefore, the biomarker panel of the present invention is useful for predicting recurrence at an early time in ovarian cancer patient population whose CA125 values are within the normal range.

The amino acid sequences of the ten polypeptide marker peptide antigens included in the present invention are listed in Table 3. More detailed description of the marker antigens is provided in Table 4. Among these marker antigens, one of the antigens (Mec1_4B7) represents a polypeptide epitope of a known gene product, histidyl t-RNA synthetase. Histidyl-tRNA synthetase (HARS) also known as histidine-tRNA ligase, is an enzyme which in humans is encoded by the HARS gene. The protein encoded by this gene is a cytoplasmic enzyme which belongs to the class II family of aminoacyl tRNA synthetases (37). Autoantibodies to histidyl t-RNA synthetase, termed as anti-Jo-1, or to other amino acyl t-RNA synthetase occur in 25% of patients with PM and dermatomyositis (38). Iavazzo and colleagues presented a case report for a patient who developed PM after she was treated for ovarian carcinoma recurrence (39). In general, PM appears to arise in cancer patients prior to diagnosis (40, 41).

TABLE 3

Properties of marker antigens included in the present invention

| Antigen | Epitope/ Mimotope | Peptide Sequence | Description of the genes that are in-frame with T7 10B gene | Size of the peptide |
|---|---|---|---|---|
| Mec1_4B7 | Epitope | EVDVRREDLVEEIKRRTGQPLCIC (SEQ ID NO: 1) | NM_002109.3, Homo sapiens histidyl-tRNA synthetase (HARS), mRNA | 24 AA |
| Mec1_4H4 | Mimotope | PGCSTTLS (SEQ ID NO: 2) | | 8 AA |
| Mec1_5H6 | Mimotope | NSFLMTSSKPR (SEQ ID NO: 3) | | 11 AA |
| Mec1_1B4 | Mimotope | ENVLVQTN (SEQ ID NO: 4) | | 8 AA |
| Mec1_2B3 | Mimotope | ELHN (SEQ ID NO: 5) | | 10 AA |
| Mec1_2H1 | Mimotope | LGSDERRHRAP (SEQ ID NO: 6) | | 11 AA |
| Mec1_3D5T | Mimotope | VDEEDMMNQVLQRSIIDQ (SEQ ID NO: 7) | | 18 AA |

TABLE 3-continued

Properties of marker antigens included in the present invention

| Antigen | Epitope/ Mimotope | Peptide Sequence | Description of the genes that are in-frame with T7 10B gene | Size of the peptide |
|---|---|---|---|---|
| Mec1_3D7 | Mimotope | VQAQQRSAPARAARAGHPEAGAGMEGAG (SEQ ID NO: 8) | | 28 AA |
| Mec1_4E8 | Mimotope | PKTMTQNSFG (SEQ ID NO: 9) | | 10 AA |
| Mec1_5A3 | Mimotope | YACLKD (SEQ ID NO: 10) | | 6 AA |

TABLE 4

Description of ten marker antigens of the present invention

| Marker Antigen | Description of genes that are in-frame with T7 10B gene | Peptide Epitope/Mimotopes, Size of the peptide in frame with T7 10 B gene | Description of the sequences that Mimotopes mimic | Unigene # | Region of similarity of AA | Antigen expression in any type of cancer |
|---|---|---|---|---|---|---|
| Mecl_4B7 | NM_002109.3, Homo sapiens histidyl-tRNA synthetase (HARS), mRNA | Epitope EVDVRREDLVEEIKRRTGQPLCIC (SEQ ID NO: 1) 24 AA | N/A | Hs.528050 | 486-509 Score = 82.5 bits (187), Expect = 2e-18 Identities = 24/24 (100%), Positives = 24/24 (100%), Gaps = 0/24 (0%) Query 1 EVDVRREDLVEEIKRRTGQPLCIC 24 Sbjct 486 EVDVRREDLVEEIKRRTGQPLCIC 509 | Autoantibodies to histidyl t RNA synthetase were shown to be present in patients diagnosed with polymyositis or dermatomyositis [38]. |
| Mecl_5H6 | ref\|NT_034772.6\|, Homo sapiens chromosome 5 genomic contig. GRCh37.p5 | Mimotope NSFLMTSSKPR (SEQ ID NO: 3) 11 AA | sp\|O95944.2\| NCTR2 HUMAN Natural cytotoxicity triggering receptor 2 | Hs.194721 | 66-73 Score = 23.5 bits (48), Expect 0.035 Identities = 7/8 (88%), Positives = 7/8 (88%), Gaps = 0/8 (0%) Query 4 LMTSSKPR 11 L TSSKPR Sbjct 66 LVTSSKPR 73 | They cytolytic effect of natural killer cells in killing the neuroblastoma target cells is mediated by natural cytotoxicity tiggering receptor 2 [43]. |
| Mecl_4H4 | NM_014671.2, Homo sapiens ubiquitin protein ligase E3C (UBE3C), mRNA | Mimotope PGCSTTLS (SEQ ID NO: 2) 8 AA | sp\|O94966.2\| UBP19 HUMAN, Ubiquitin carboxyl-terminal hydrolase 19 | Hs.721972 | 887-894 Score = 18.9 bits (37), Expect = 0.88 Identities = 6/8 (75%), Positive = 6/8 (75%), Gaps = 0/8 (0%) Query 1 PGCSTTLS 8 PGC T LS Sbjct 887 PGCTTLLS 894 | Ubiquitin carboxyl-terminal hydrolase 1 was reported as tumor supressor and biomarker for hepatocellular carcinoma [44]. |
| Mecl_1B4 | No significant similarity | Mimotope ENVLVQTN (SEQ ID NO: 4) 8 AA | sp\|Q9C026.1\| TRIM9 HUMAN, E3 ubiquitin-protein ligase TRIM9 | Hs.733171 | 36-41 Score = 19.7 bits (39), Expect = 0.47 Identities = 5/6 (83%), Positives = 6/6 (100%), Gaps = 0/6 (0%) Query 2 NVLVQT 7 N+LVQT Sbjct 36 NILVQT 41 | Trim proteins are important regulators of carcinogenesis [45]. |
| Mecl_2B3 | NM_001195045, Homo sapiens Yes-associated protein 1 (YAP1), transcript variant 4, mRNA | Mimotope ELHN 4 AA | sp\|P07711.2\| CATL1 HUMAN, Cathepsin L1 | Hs.731507 | 60-63 Score = 16.8 bits (32), Expect = 0.95 Identities = 4/4 (100%), Positives = 4/4 (100%), Gaps = 0/4 (0%) Query 1 ELHN 4 ELHN Sbjct 10 ELHN 63 | Cathepsin L plays a potential role in glioblastoma invasion (5). |

TABLE 4-continued

Description of ten marker antigens of the present invention

| Marker Antigen | Description of genes that are in-frame with T7 10B gene | Peptide Epitope/Mimotopes, in-frame with T7 10 B gene | Size of the peptide | Description of the sequences that Mimotopes mimic | Unigene # | Region of similarity of AA | Antigen expression in any type of cancer |
|---|---|---|---|---|---|---|---|
| Mec1_2H1 | NR_003287.2, Homo sapiens RNA, 28S ribosomal 1 (RN28S1), ribosomal RNA | Mimotope LGSDERRHRAP (SEQ ID NO: 6) | 11 AA | sp\|Q8WVS4.3\| WDR60 HUMAN, WD repeat-containing protein 60 | Hs.609371 | 212-218 Score = 21.0 bits (42), Expect = 0.29 Identities = 6/7 (86%), Positives = 6/7 (86%), Gaps = 0/7 (0%) Query 5 ERRHRAP 11 ERRHR P Sbjct 212 ERRHRKP 218 | Bromo-domain and WD repeat-containing protein 3 are reported to be elevated in breast cancer [47]. |
| Mec1_3D5T | NM_018683.3, Homo sapiens ring finger protein 114 (RNF114), mRNA | Epitope VDEEDMMNQVLQRSIIDQ (SEQ ID NO: 7) | 18 AA | N/A | Hs.144949 | 211-228 Score = 64.7 bits (145), Expect = 3e-15 Identities = 18/18 (100%), Positives = 18/18 (100%), Gaps = 0/18 (0%) Query 1 VDEEDMMNQVLQRSIIDQ 18 VDEEDMMNQVLQRSIIDQ Sbjct 211 VDEEDMMNQVLQRSIIDQ 228 | Ring finger protein RNF 19-A is reported as a relevant biomarker for prostate cancer detection [48]. |
| Mec1_3D7 | NM_014762.3, Homo sapiens 24-dehydrocholesterol reductase (DHCR24), mRNA | Mimotope VQAQQRSAPARAARAGHP EAGAGMEGAG (SEQ ID NO: 8) | 28 AA | sp\|Q2T9J0.3\| TYSD1 HUMAN, Peroxisomal leader peptide-processing protease | Not found | 21-30 Score = 26.5 bits (55), Expect = 0.052 Identities = 8/10 (80%), Positives = 9/10 (90%), Gaps = 0/10 (0%) Query 12 AARAGHPEAG 21 A RAG+PEAG Sbjct 21 ASRAGQPEAG 30 | No relevance in cancer |
| Mec1_4E8 | NM_001113239.2, Homo sapiens homeodomain interacting protein kinase 2 (HIPK2), transcript variant 2, mRNA | Mimotope PKTMTQNSFG (SEQ ID NO: 9) | 10 AA | sp\|Q4G0N0.2\| GGTA1 HUMAN, Glycoprotein alpha-galactosyl-transferase | Hs.97469 | 86-92 Score = 21.8 bits (44), Expect = 0.12 Identities = 6/7 (86%), Positives = 6/7 (86%), Gaps = 0/7 (0%) Query 4 MTQNSFG 10 MTQ SFG Sbjct 86 MTQQSFG 92 | Galactosyl transferases are novel tumor biomarkers for gynecological cancers [49]. |
| Mec1_5A3 | NR_003286.2, Homo sapiens ribosomal 1 (RN18S1), ribosomal RNA | Mimotope YACLKD (SEQ ID NO: 10) | 6 AA | sp\|Q14541.3\| HNF4G HUMAN, Hepatocyte nuclear factor (HNF) 4-gamma | Hs.241529 | 237-241 Score = 20.2 bits (40), Expect = 0.17 Identities = 5/5 (100%), Positives = 5/5 (100%), Gaps = 0/5 (0%) Query 1 YACLK 5 YACLK Sbjct 237 YACLK 241 | Deregulation of HNF 4 alpha is associated with hepatocellular carcinoma progression [50]. |

The polypeptide marker antigens Mec1_5H6 and Mec1_4H4 each contain an open reading frame with the T7 10B gene with a frameshift within the natural reading frame of the gene (Table 4). These polypeptides are termed as mimotopes because they mimic linear or conformational epitopes of an immunogen (21, 22).

Although autoantibodies to TAAs develop at the early onset of the disease, only a few have been evaluated as prognostic biomarkers because very little data on the evidence of tumor autoantibodies in monitoring disease or predicting recurrence in ovarian cancer patients are available. Reports from Vogl and colleagues (23) revealed 46% prevalence of circulating p53 autoantibodies in a study population comprising 83 OVCA patients. Their study also indicated that in a bivariate analysis, patients with anti-p53 autoantibodies had a 1.96-fold risk for relapse (95% confidence interval 1.02-3.78).

Polypeptide marker antigens indicating a poor response to therapy at an early time point provide a clinician with information helpful in making decisions about modifying patient treatment. Such modifications could include prolonging first-line treatment, initiating maintenance treatment, or early second-line treatment of recurrent disease. These better-informed treatment modifications should result in more durable response and greater survival among OVCA patients. There has been considerable debate on the beneficial outcome of OVCA patients from the recommencement of early chemotherapy treatment due to a rise in CA125 values during their disease monitoring phase after the completion of therapy.

While illustrative embodiments of the invention have been disclosed herein, it is understood that other embodiments and modifications may be apparent to those of ordinary skill in the art.

REFERENCES

1. Schink J C (1999) Current initial therapy of stage III and IV ovarian cancer: challenges for managed care. *Semin Oncol* 26: 2-7.
2. Mutch D G (2002) Surgical management of ovarian cancer. *Semin Oncol* 29: 3-8.
3. Schwartz P E (2002) Current diagnosis and treatment modalities for ovarian cancer. *Cancer Treat Res* 107: 99-118.
4. Chua T C, Liauw W, Robertson G, Morris D L (2010) Second-line treatment of first relapse recurrent ovarian cancer. *Aust N Z J Obstet Gynaecol* 50: 465-71.
5. Mann W J, Patsner B, Cohen H, Loesch M (1988) Preoperative serum CA125 levels in patients with surgical stage I invasive ovarian adenocarcinoma. *J Natl Cancer Inst* 80: 208-9.
6. Redman C W, Blackledge G R, Kelly K, Powell J, Buxton E J, Luesley D M (1990) Early serum CA125 response and outcome in epithelial ovarian cancer. *Eur J Cancer* 26: 593-6.
7. van der Burg M E, Lammes F B, Verweij J (1990) The role of CA 125 in the early diagnosis of progressive disease in ovarian cancer. *Ann Oncol* 1: 301-2.
8. Krivak T C, Tian C, Rose G S, Armstrong D K, Maxwell G L (2009) A Gynecologic Oncology Group Study of serum CA125 levels in patients with stage III optimally debulked ovarian cancer treated with intraperitoneal compared to intravenous chemotherapy: an analysis of patients enrolled in GOG 172. *Gynecol Oncol* 115:81-5.
9. Wilder J L, Pavlik E, Straughn J M et al. (2003) Clinical implications of a rising serum CA125 within the normal range in patients with epithelial ovarian cancer: a preliminary investigation. *Gynecol Oncol* 89: 233-5.
10. Anastasi E, Marchei G G, Viggiani V, Gennarini G, Frati L, Reale M G (2010) HE4: a new potential early biomarker for the recurrence of ovarian cancer. *Tumour Biol* 31: 113-9.
11. Schorge J O, Drake R D, Lee H et al. (2004) Osteopontin as an adjunct to CA125 in detecting recurrent ovarian cancer. *Clin Cancer Res* 10: 3474-8.
12. Tassi R A, Calza S, Ravaggi A et al. (2009) Mammaglobin B is an independent prognostic marker in epithelial ovarian cancer and its expression is associated with reduced risk of disease recurrence. *BMC Cancer* 9: 253.
13. Havrilesky L J, Whitehead C M, Rubatt J M et al. (2008) Evaluation of biomarker panels for early stage ovarian cancer detection and monitoring for disease recurrence. *Gynecol Oncol* 110: 374-82.
14. Wysham W Z, Mhawech-Fauceglia P, Li H, Hays L, Syriac S, et al. (2012) BRCAness Profile of Sporadic Ovarian Cancer Predicts Disease Recurrence. *PLoS ONE* 7(1): e30042.
15. Li Y, Karjalainen A, Koskinen H et al. (2005) p53 autoantibodies predict subsequent development of cancer. *Int J Cancer* 114: 157-60.
16. Draghici S, Chatterjee M, Tainsky M A (2005) Epitomics: serum screening for the early detection of cancer on microarrays using complex panels of tumor antigens. *Expert Rev Mol Diagn* 5: 735-43.
17. Chatterjee M, Mohapatra S, Ionan A et al. (2006) Diagnostic markers of ovarian cancer by high-throughput antigen cloning and detection on arrays. *Cancer Res* 66: 1181-90.
18. Vogl F D, Stickeler E, Weyermann M et al. (1999) p53 autoantibodies in patients with primary ovarian cancer are associated with higher age, advanced stage and a higher proportion of p53-positive tumor cells. *Oncology* 57: 324-9.
19. Heubner M, Errico D, Kasimir-Bauer S, Herlyn D, Kimmig R, Wimberger P (2011) EpCAM-autoantibody levels in the course of disease of ovarian cancer patients. *Med Oncol* 28: 626-30.
20. Geysen H M, Rodda S J, Mason T J (1986) A priori delineation of a peptide which mimics a discontinuous antigenic determinant. *Mol Immunol* 23: 709-15.
21. Van Regenmortel M H V. Molecular dissection of protein antigens and the prediction of epitopes. In: Van Regenmortel M H V, Muller S (eds) Synthetic Peptides as Antigens. Amsterdam, Elsevier, 1999: pp. 1-78.
22. Meloen R H, Puijk W C, Slootstra J W (2000) Mimotopes: realization of an unlikely concept. *J Mol Recognit* 13: 352-9.
23. Hoess R, Brinkmann U, Handel T, Pastan I (1993) Identification of a peptide which binds to the carbohydrate-specific monoclonal antibody B3. *Gene* 128: 43-9.
24. Oldenburg K R, Loganathan D, Goldstein I J, Schultz P G, Gallop M A (1992) Peptide ligands for a sugar-binding protein isolated from a random peptide library. *Proc Natl Acad Sci USA* 89: 5393-7.
25. Tumenjargal S, Gellrich S, Linnemann T et al. (2003) Anti-tumor immune responses and tumor regression induced with mimotopes of a tumor-associated T cell epitope. *Eur J Immunol* 33: 3175-85.
26. Kieber-Emmons T, Luo P, Qiu J et al. (1999) Vaccination with carbohydrate peptide mimotopes promotes anti-tumor responses. *Nat Biotechnol* 17: 660-5.
27. Etzioni R, Urban N, Ramsey S et al. (2003) The case for early detection. *Nat Rev Cancer* 3: 243-52.

28. Makawita S, Diamandis E P (2010) The bottleneck in the cancer biomarker pipeline and protein quantification through mass spectrometry-based approaches: current strategies for candidate verification. *Clin Chem* 56: 212-22.
29. Mishra, A., Verma, M. Cancer Biomarkers: Are We Ready for the Prime Time? *Cancers* 2010, 2, 190-208.
30. Rustin G J, Nelstrop A E, Tuxen M K, Lambert H E (1996) Defining progression of ovarian carcinoma during follow-up according to CA 125: a North Thames Ovary Group Study. *Ann Oncol* 7: 361-4.
31. Rustin G J, van der Burg M E, Griffin C L et al. (2010) Early versus delayed treatment of relapsed ovarian cancer (MRC OV05/EORTC 55955): a randomized trial. *Lancet* 376: 1155-63.
32. Diefenbach C S, Gnjatic S, Sabbatini P et al. (2008) Safety and immunogenicity study of NY-ESO-1b peptide and montanide ISA-51 vaccination of patients with epithelial ovarian cancer in high-risk first remission. *Clin Cancer Res* 14: 2740-8.
33. Gadducci A, Ferdeghini M, Buttitta F et al. (1999) Assessment of the prognostic relevance of serum anti-p53 antibodies in epithelial ovarian cancer. *Gynecol Oncol* 72: 76-81.
34. Kim S, Cho H, Nam E J et al. (2010) Autoantibodies against stress-induced phosphoprotein-1 as a novel biomarker candidate for ovarian cancer. *Genes Chromosomes Cancer* 49: 585-95.
35. Naora H, Yang Y Q, Montz F J, Seidman J D, Kurman R J, Roden R B (2001) A serologically identified tumor antigen encoded by a homeobox gene promotes growth of ovarian epithelial cells. *Proc Natl Acad Sci USA* 98: 4060-5.
36. Odunsi K, Jungbluth A A, Stockert E et al. (2003) NY-ESO-1 and LAGE-1 cancertestis antigens are potential targets for immunotherapy in epithelial ovarian cancer. *Cancer Res* 63: 6076-83.
37. Wasmuth J J, Garlock L R. Chromosomal localization of human gene for histidyl-tRNA synthetase: clustering of genes encoding aminoacyl-tRNA synthetases on human chromosome 5. *Somat Cell Mol Genet* 1986; 12:513-517.
38. Howard O M, Dong H F, Yang D, Raben N, Nagaraju K, Rosen A, et al. Histidyl-tRNA synthetase and asparaginyl-tRNA synthetase, autoantigens in myositis, activate chemokine receptors on T lymphocytes and immature dendritic cells. *J Exp Med* 2002; 196:781-791.
39. Iavazzo C, Vorgias G, Papadakis M, Manikis P, Mavromatis I, Akrivos T. Polymyositis in a patient with recurring ovarian cancer and history of unrelated breast cancer. Arch Gynecol Obstet 2007; 276:81-84.
40. Ghosh A, Malak T M, Pool A J. Polymyositis and ovarian carcinoma: a case report. Arch Gynecol Obstet 2007; 275:195-197.
41. Sigurgeirsson B, Lindelof B, Edhag O, Allander E. Risk of cancer in patients with dermatomyositis or polymyositis. A population-based study. N Engl J Med 1992; 326:363-367.
42. Morris R T, Monk B J. Ovarian cancer: relevant therapy, not timing, is paramount. *Lancet* 2010; 376:1120-1122.
43. Sivori S, Parolini S, Marcenaro E, Castriconi R, Pende D, Millo R, et al. Involvement of natural cytotoxicity receptors in human natural killer cell-mediated lysis of neuroblastoma and glioblastoma cell lines. *J Neuroimmunol* 2000; 107:220-225.
44. Yu J, Tao Q, Cheung K F, Jin H, Poon F F, Wang X, et al. Epigenetic identification of ubiquitin carboxyl-terminal hydrolase L1 as a functional tumor suppressor and biomarker for hepatocellular carcinoma and other digestive tumors. *Hepatology* 2008; 48:508-518.
45. Hatakeyama S, TRIM proteins and cancer. *Nat Rev Cancer* 2011; 11: 792-804.
46. Vitorino R, Alves R, Barros A, Caseiro A, Ferreira R, Lobo M C, Bastos A, Duarte J, Carvalho D, Santos L L, Amado F L. Finding new posttranslational modifications in salivary proline-rich proteins. *Proteomics* 2010; 10:3732-3742.
47. Suh E J, Kabir M H, Kang U B, Lee J W, Yu J, Noh D Y, Lee C. Comparative profiling of plasma proteome from breast cancer patients reveals thrombospondin-1 and BRWD3 as serological biomarkers. *Exp Mol Med* 2012; 44: 36-44.
48. Bai V U, Hwang O, Divine G W, Barrack E R, Menon M, Reddy G P, Hwang C. Averaged differential expression for the discovery of biomarkers in the blood of patients with prostate cancer, *PLoS One* 2012; 7:e34875.
49. Seko A, Kataoka F, Aoki D, Sakamoto M, Nakamura T, Hatae M, Yonezawa S, Yamashita K. Beta1,3-galactosyltransferases-4/5 are novel tumor markers for gynecological cancers, *Tumour Biol* 2009; 30: 43-50.
50. Lazarevich N L, Shavochkina D A, Fleishman D I, Kustova I F, Morozova O V, Chuchuev E S, Patyutko Y I. Deregulation of hepatocyte nuclear factor 4 (HNF4) as a marker of epithelial tumors progression. *Exp Oncol* 2010; 32:167-171.
51. J. Sambrook, E. F. Fritsch, and T. Maniatis, 1989, Molecular Cloning, A Laboratory Manual, 2d edition, Cold Spring Harbor, N.Y.
52. Current protocols in molecular biology, "Chapter 16: Protein Expression". F. M. Ausbel, et al. eds John Wiley & Sons, New York, 1994-2000.
53. Varma M M, Nolte D D, Inerowicz H D, Regnier F E. Spinning-disk self-referencing interferometry of antigen-antibody recognition. Optics Lett. 29: 950-952 (2004).
54. Khandadash R, Partouche S, Weiss A, et al. A Fully Synthetic "Phage-Like" System II: Synthesis and Live Cell Screening of Combinatorial Libraries of Peptides on Sub-Cellular Sized Microspheres. Open Optics J. 5 (Suppl 1-M3): 17-27 (2011).
55. Prestiagiacomo T, R. L. Humbel R L, Larida B, Binder S R. Multiplexed analysis of thirteen autoantibodies using the Bioplex 2200 fully automated immunoassay analyzer, in From Animal Models to Human Genetics: Research on the Induction of Pathenogenicity of Autoantibodies, K. Conrad et al., eds. (Pabst Science Publishers, Lengerich, 2004), pp. 463-466.
56. Castel G, Chtèoui M, Heyd B, Tordo N. Phage Display of Combinatorial Peptide Libraries: Application to Antiviral Research. Molecules 16: 3499-3518 (2011).
57. Zhang H, et al. Peptide Epitopes Recognized by a Human Anti-Cryptococcal Glucuronoxylomannan Antibody. Immun. 65: 1158-1164 (1997).
58. Buchwald U K, et al. A Peptide Mimotope of Type 8 Pneumococcal Capsular Polysaccharide Induces a Protective Immune Response in Mice. Infect. Immun 75: 325-333 (2005)
59. Ganglberger E, et al. Allergen mimotopes for 3-dimensional epitope search and induction of antibodies inhibiting human IgE. FASEB J. 14: 2177-2184 (2000).
60. Fung-Kee-Fung M, Oliver T, Elit L, Oza A, Hirte H W, Bryson P. Optimal chemotherapy treatment for women with recurrent ovarian cancer. Curr Oncol 14:195-208 (2007).
61. Harlow E and Lane D. Antibodies: A Laboratory Manual. Cold Spring Harbor Laboratory, Cold Spring Harbor, 1988.

What is claimed is:

1. A method for detecting the presence of autoantibody biomarkers, including the steps of:
    collecting a sample of serum from a recurrent ovarian cancer patient;
    exposing the sample of serum to a polypeptide marker antigen of SEQ ID NO: 8, the polypeptide marker antigen binding specifically to an autoantibody biomarker; and
    quantitating the specific binding of an autoantibody biomarker by the polypeptide marker antigen.

2. The method of claim 1, wherein the quantitating step further includes the steps of indicating the binding of the autoantibody biomarker by the polypeptide marker antigen with a signal generating system, and analyzing the signals produced by the signal generating system with a signal analysis system.

3. The method of claim 1, additionally including the step of administering treatment for recurrent ovarian cancer to the recurrent ovarian cancer patient.

4. A method for detecting the presence of an autoantibody biomarker in a patient suspected of having recurrent ovarian cancer, including the steps of:
    collecting a sample of serum from the patient;
    exposing the sample of serum to a polypeptide marker antigen SEQ ID NO: 8, the polypeptide marker antigen binding specifically to an autoantibody biomarker;
    quantitating the specific binding of an autoantibody biomarker by the polypeptide marker antigen; and
    detecting the presence of the autoantibody biomarker in the sample of body fluid.

5. The method of claim 4, wherein the quantitating step further includes the steps of indicating the binding of the autoantibody biomarker by the polypeptide marker antigen with a signal generating system, and analyzing the signals produced by the signal generating system with a signal analysis system.

* * * * *